United States Patent
McClendon et al.

[11] Patent Number: 5,717,603
[45] Date of Patent: Feb. 10, 1998

[54] INTEGRATED TEST STATION FOR TESTING LIQUID FLOW AND ELECTRICAL SAFETY CHARACTERISTICS OF IV PUMPS

[75] Inventors: Robert R. McClendon, Peoria; Aleandro DiGianfilippo, Scottsdale, both of Ariz.; Leon Huang, Hoffman Estates, Ill.

[73] Assignee: Spectrel Partners, L.L.C., Phoenix, Ariz.

[21] Appl. No.: 671,089

[22] Filed: Jun. 27, 1996

Related U.S. Application Data

[63] Continuation of Ser. No. 293,238, Aug. 19, 1994, abandoned.

[51] Int. Cl.$^6$ .................................................. G01F 1/00
[52] U.S. Cl. .................................................. 364/510; 364/481
[58] Field of Search ........................... 364/509–510, 364/550, 558, 481, 482, 413.01, 413.11; 417/18–24, 6, 27, 28, 29–32; 604/65, 67, 81; 28/DIG. 12; 222/52, 55, 56, 57, 58, 63; 137/561 R, 594, 595

[56] References Cited

U.S. PATENT DOCUMENTS

| | | |
|---|---|---|
| 4,137,913 | 2/1979 | Georgi . |
| 4,221,543 | 9/1980 | Cosentino et al. ............ 417/22 |
| 4,308,866 | 1/1982 | Jelliffe . |
| 4,401,981 | 8/1983 | Figler . |
| 4,467,844 | 8/1984 | Di Gianfilippo et al. . |
| 4,525,163 | 6/1985 | Slavik et al. ............ 604/65 |
| 4,648,430 | 3/1987 | Di Gianfilippo et al. . |
| 4,653,010 | 3/1987 | Figler et al. . |
| 4,657,529 | 4/1987 | Prince et al. . |
| 4,670,007 | 6/1987 | Wheeldon et al. . |
| 4,705,506 | 11/1987 | Archibald ............ 604/81 |
| 4,756,706 | 7/1988 | Kerns et al. . |
| 4,769,001 | 9/1988 | Prince . |
| 5,056,568 | 10/1991 | DiGianfilippo et al. . |
| 5,112,298 | 5/1992 | Prince et al. . |
| 5,200,090 | 4/1993 | Ford et al. . |
| 5,207,642 | 5/1993 | Orkin et al. ............ 604/65 |
| 5,244,463 | 9/1993 | Cordner, Jr. et al. . |
| 5,287,859 | 2/1994 | John . |
| 5,304,126 | 4/1994 | Epstein et al. ............ 604/67 |
| 5,319,572 | 6/1994 | Wilhelm et al. ............ 364/510 |
| 5,329,459 | 7/1994 | Kaufman et al. . |
| 5,355,735 | 10/1994 | Miller et al. . |
| 5,366,346 | 11/1994 | Danby ............ 417/18 |
| 5,378,231 | 1/1995 | Johnson et al. ............ 604/67 |
| 5,438,510 | 8/1995 | Bryant et al. ............ 364/413.11 |

OTHER PUBLICATIONS

Brochure A Prior Art, medTester 1000B, (Electrical Safety Analyzer) date unknown.
Brochure B, Prior Art, medTester 5000B, (Electrical Safety Analyzer) date unknown.
Brochure C, Prior Art, Dale 600, Electrical Safety Analyzer date unknown.
Brochure D, Prior ARt, Bio–Tek Insturments, Inc. Infusion Device Anaylzer (Electrical Testing Device) date unknown.
Brochure E, Prior Art, Infutest 2000 date unknown.
Advertisement F, Prior Art, Infutest 2000 date unknown.
Brochure G, Prior Art, Infutest 2000 date unknown.
Brochure H, Prior Art, IV Infusion Pump Analyzer 404A date unknown.

*Primary Examiner*—James P. Trammell
*Attorney, Agent, or Firm*—Ryan, Maki, Mann & Hohenfeldt

[57] ABSTRACT

A testing apparatus for an intravenous pump houses a first component adapted to test at least one liquid flow characteristic of the pump and a second component adapted to be coupled electrically to the pump to test at least one electrical characteristic of the pump. An interior panel compartmentalizes the housing into two compartments isolated one from the other. The first component is confined solely within one of the compartments and the second component is confined solely within the other one of the compartments.

32 Claims, 34 Drawing Sheets

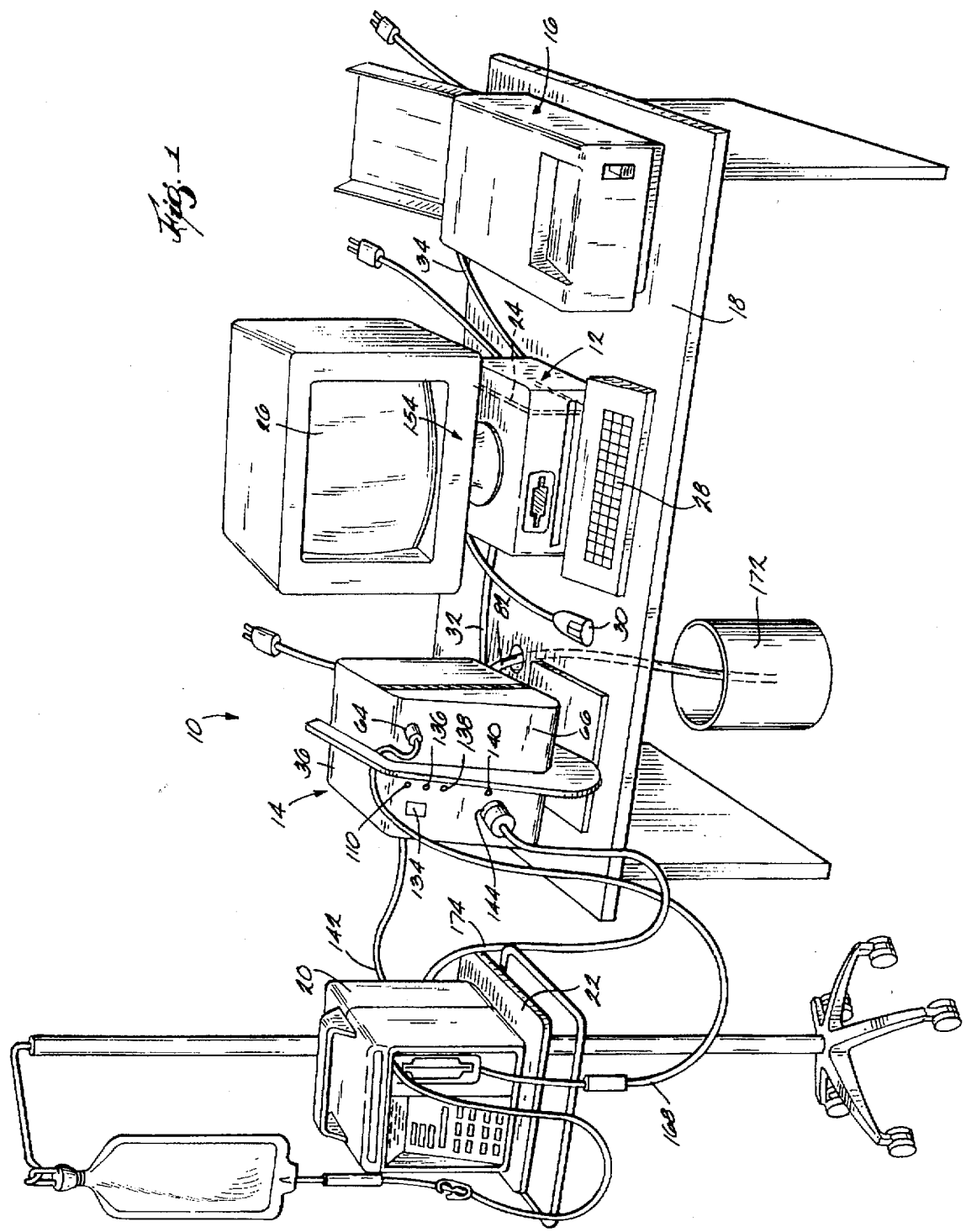

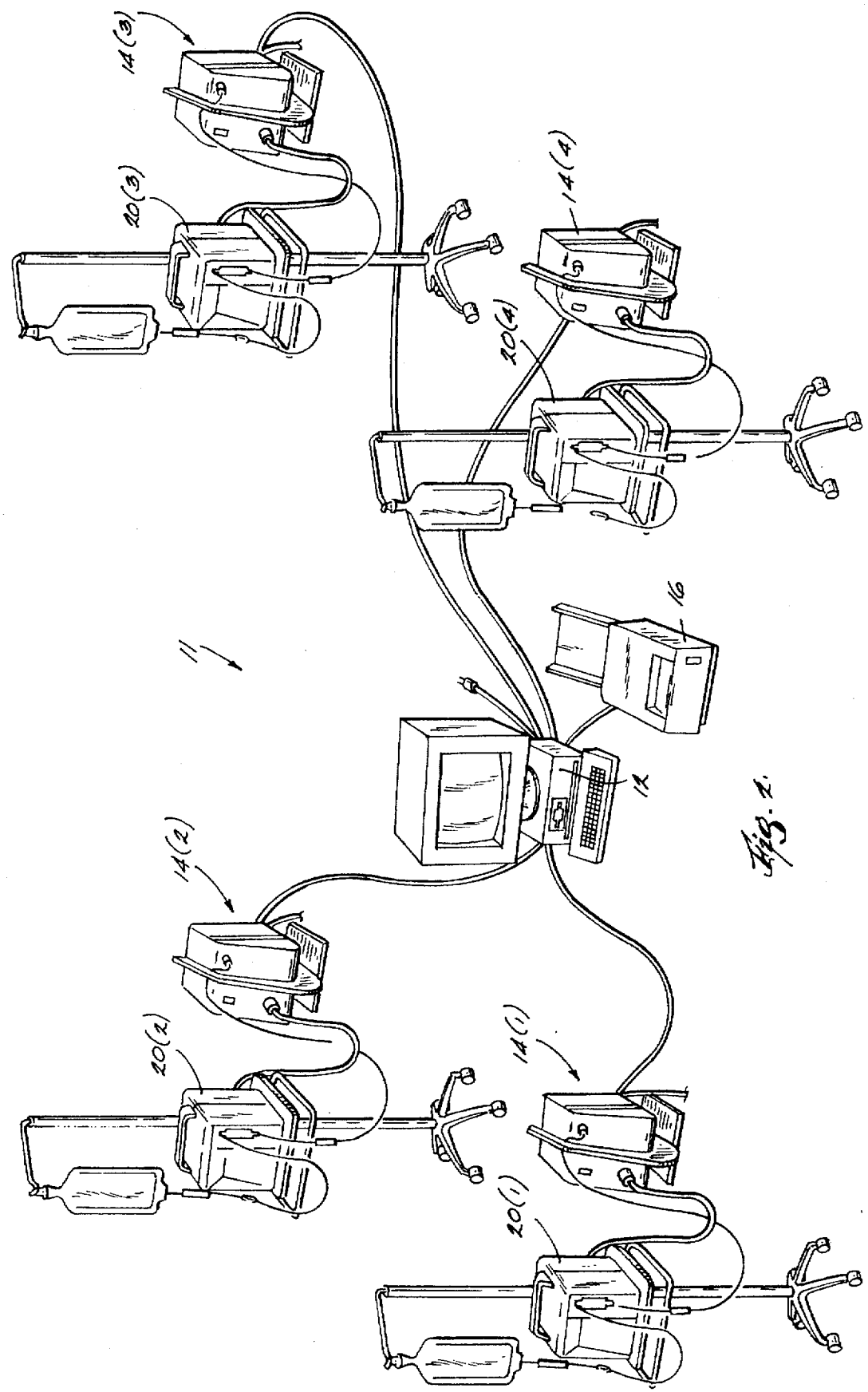

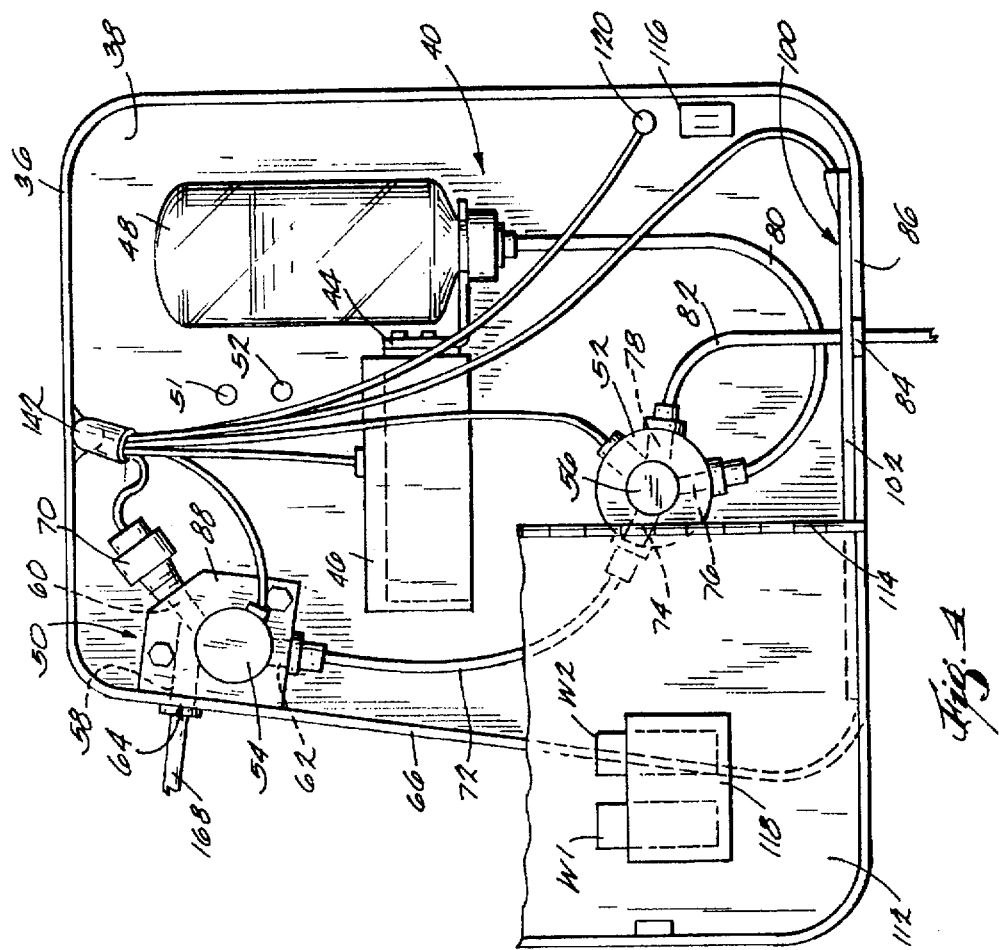
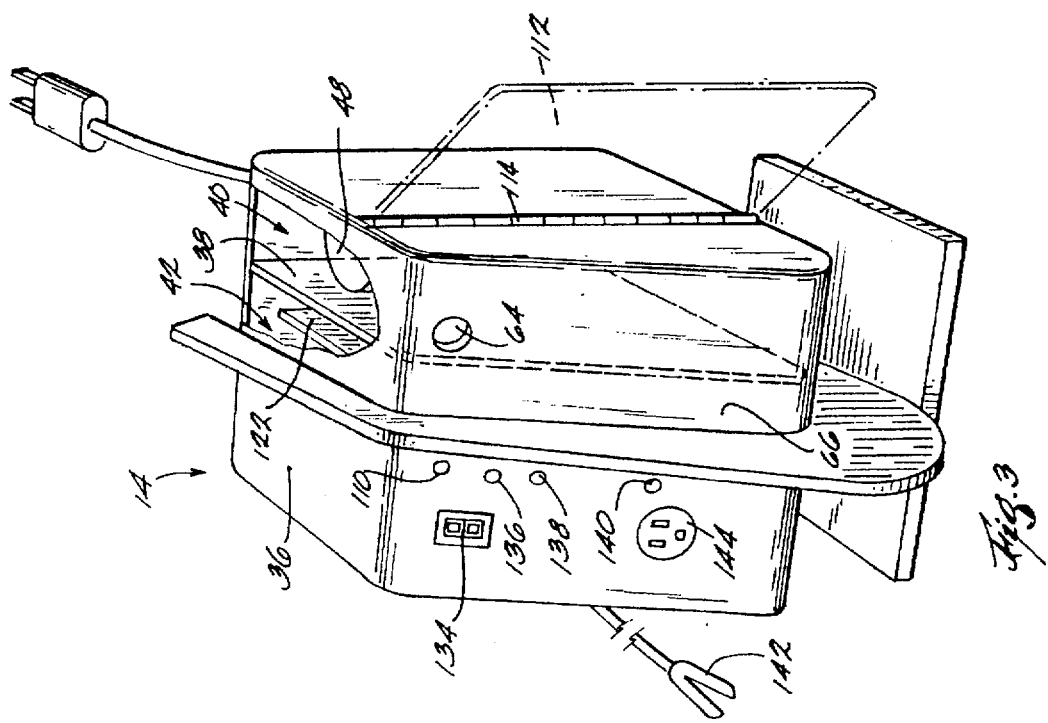

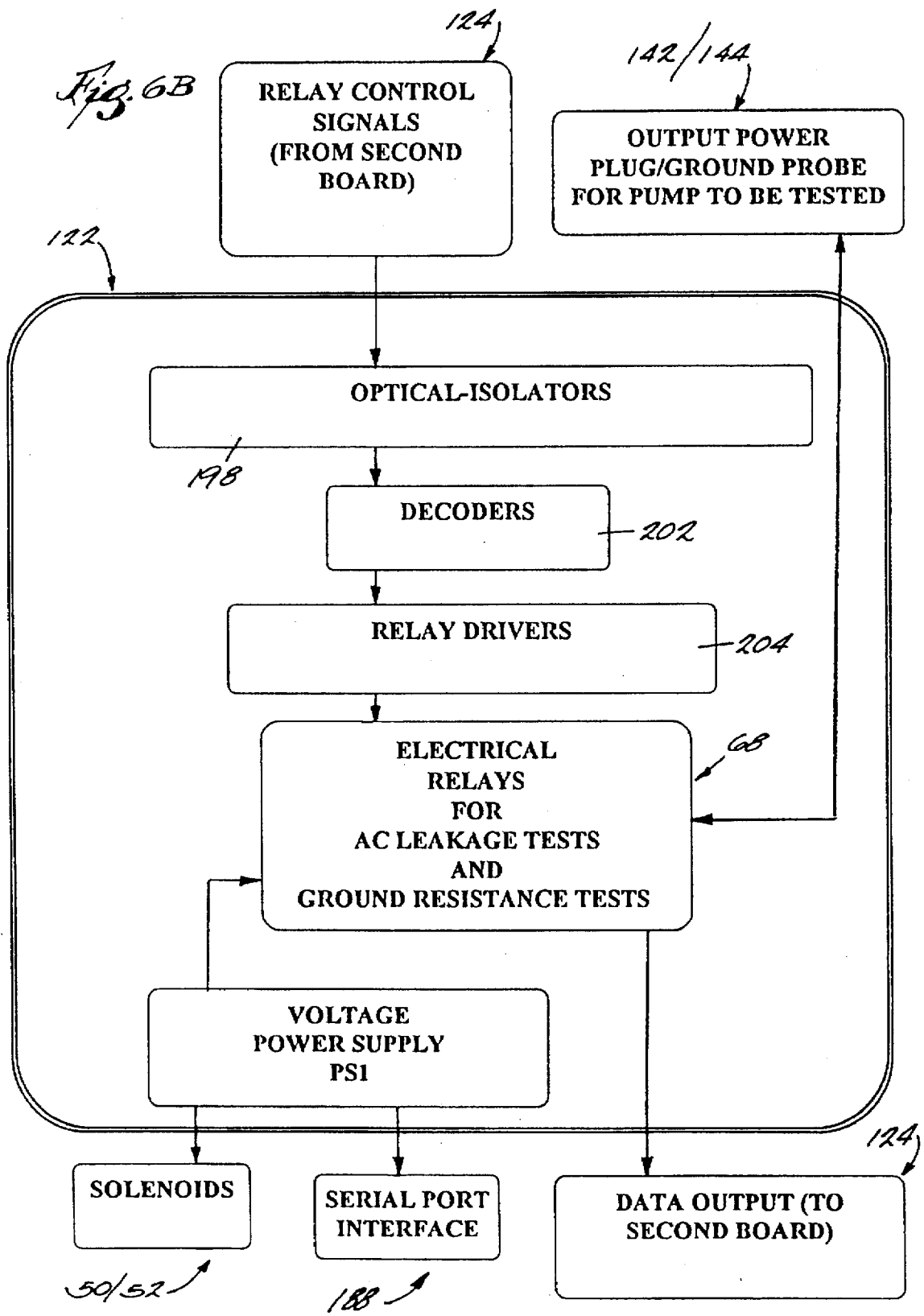

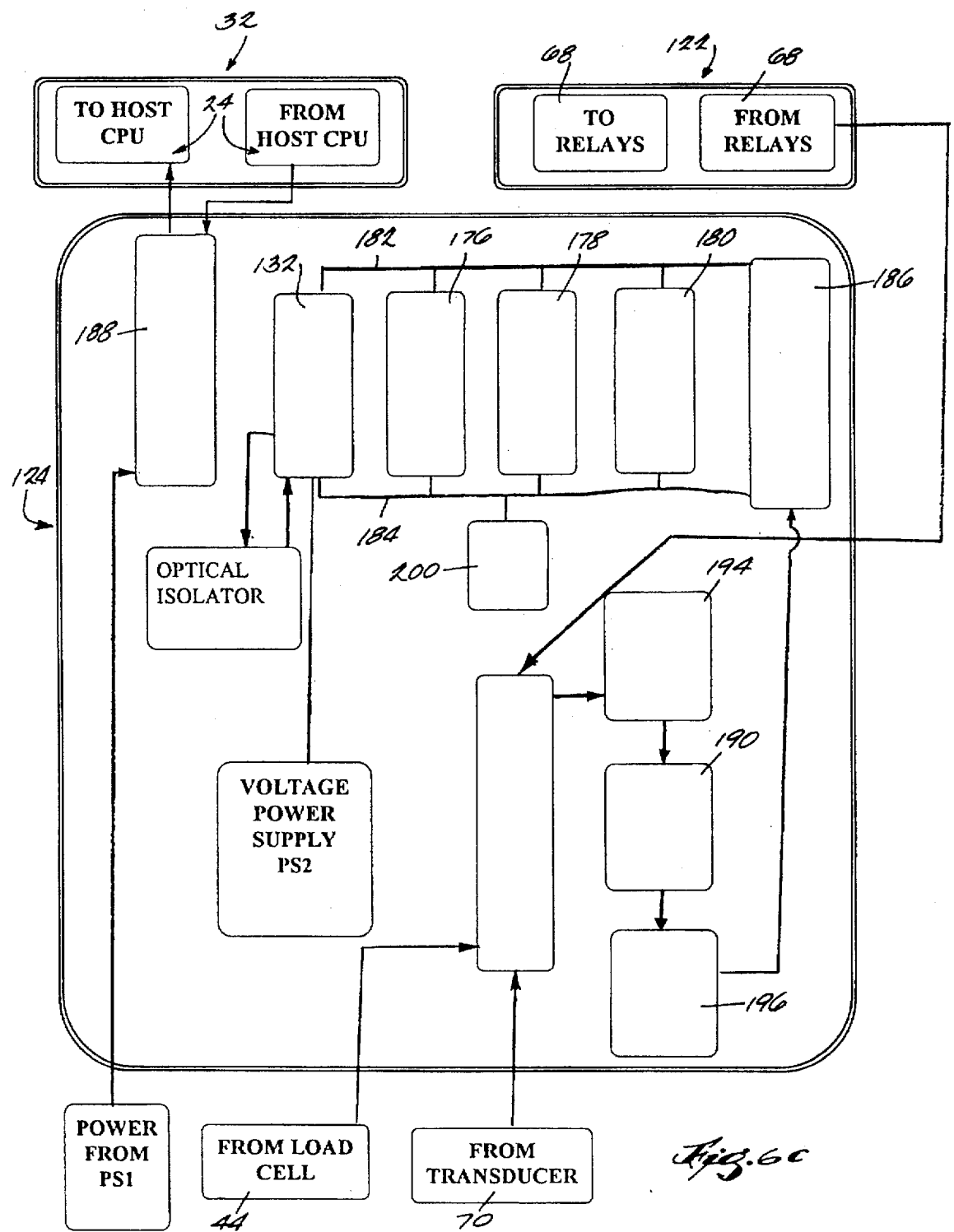

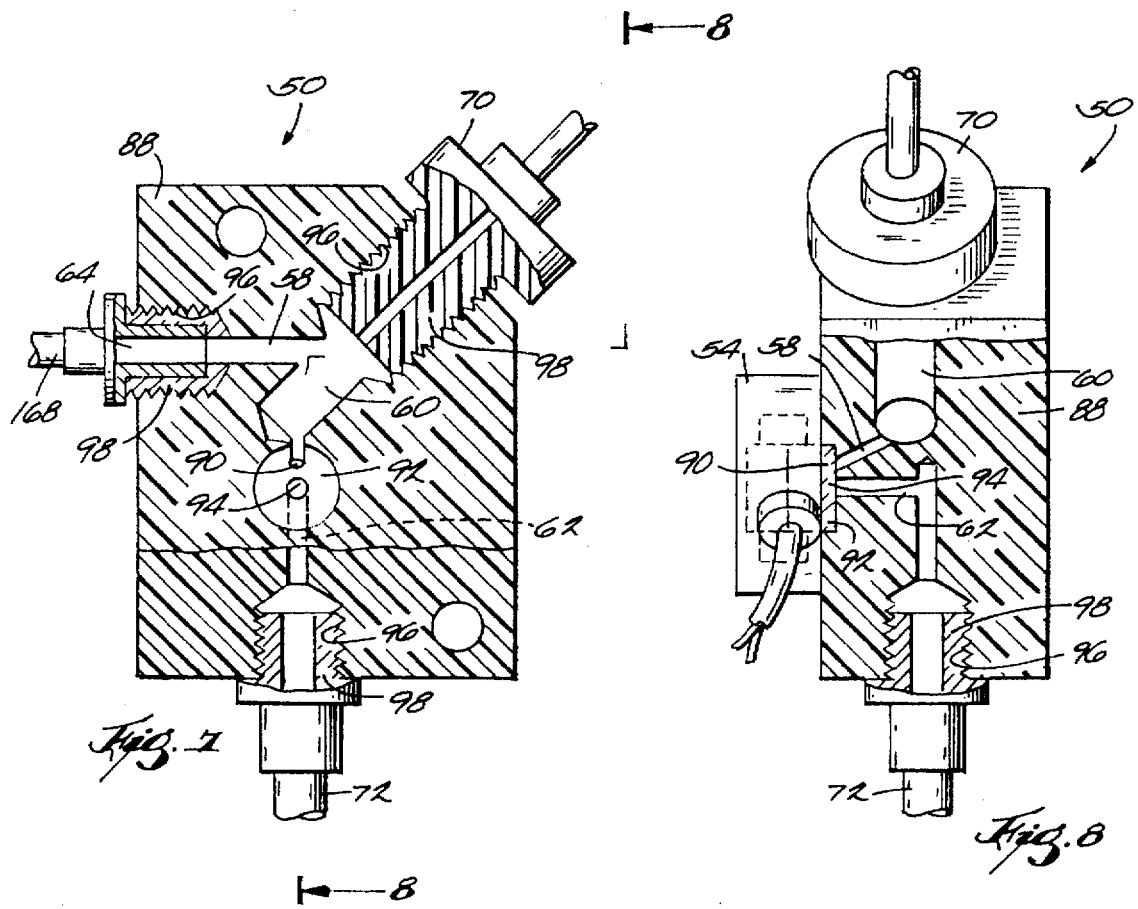
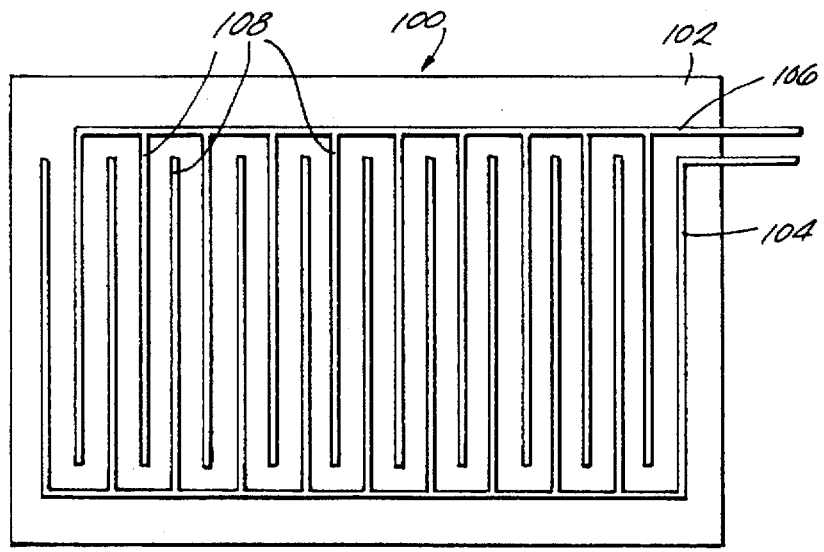

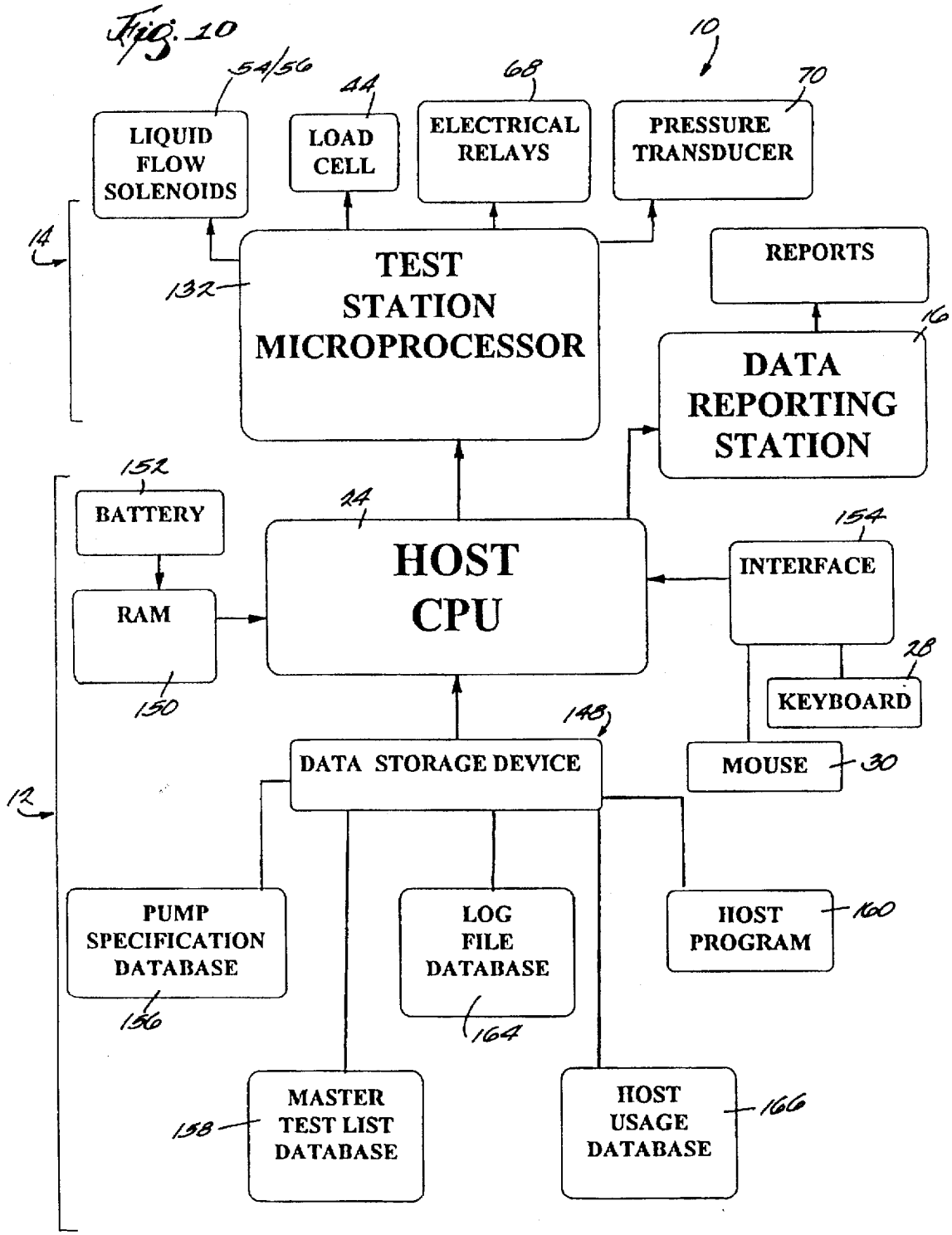

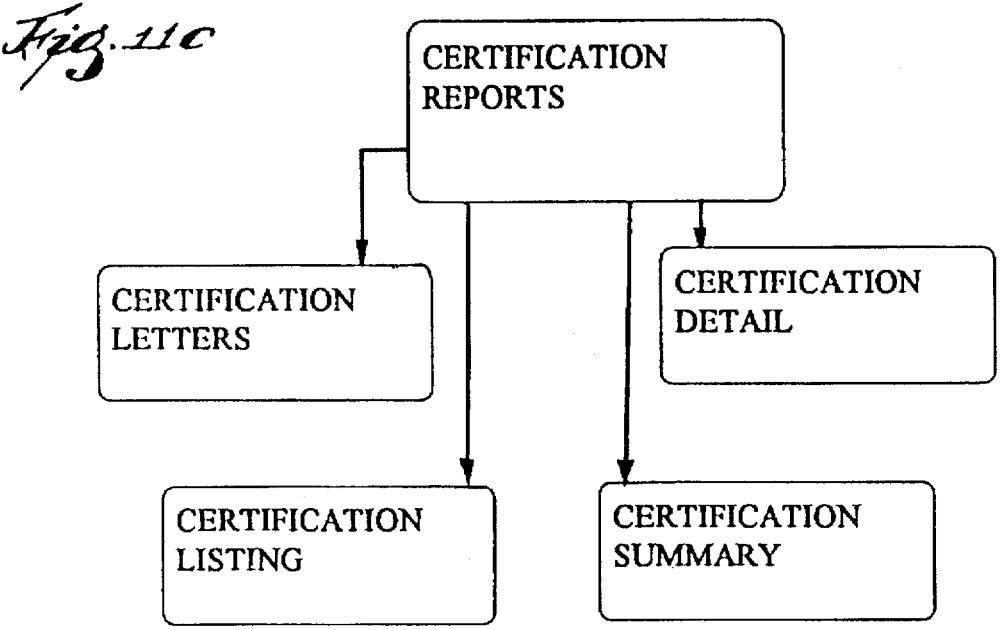
Fig. 11C
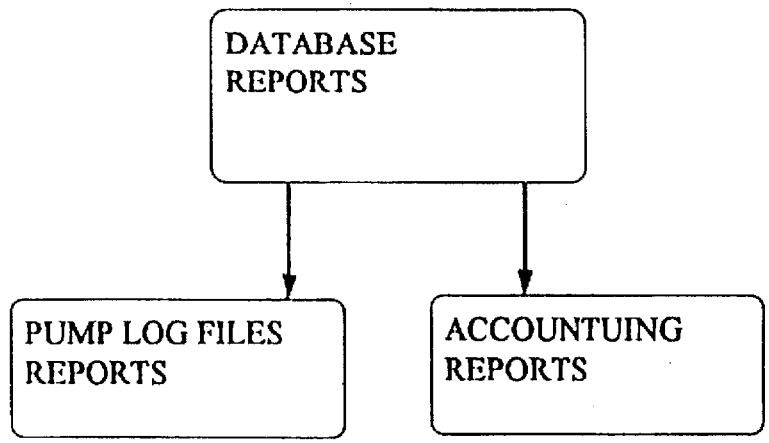

| MANUFACTURER | MODEL | SPECIFICATION VALUES ||||
|---|---|---|---|---|---|
| | | NUMBER OF PUMP CHANNELS | CHANNEL DESIGNATORS | ACCURACY FLOW RATE | FLOW RATE ACCURACY SPEC. |
| ABBOTT LABORATORIES | PROVIDER ONE | 1 | | 250 CC/HR | +/- 5% |
| | PROVIDER ONE+ | 1 | | 250 CC/HR | +/- 5% |
| | PROVIDER 2000+ | 1 | | | +/- 5% |
| | PROVIDER 4000+ | 1 | | | +/- 5% |
| | PROVIDER 5000 | 1 | | 240 CC/HR | +/- 5% |
| | PROVIDER 5500 | 1 | | 240 CC/HR | +/- 5% |
| | PROVIDER 6000 | 2 | CHANNEL A | 240 CC/HR | +/- 5% |
| | | | CHANNEL B | 240 CC/HR | +/- 5% |
| | PAIN MANAGEMENT PROVIDER | 1 | | 125 ML/HR | +/- 5% |
| PHARMACIA DELTIC | CADD-5100 | 1 | | 299 ML/24 HR | +/- 6% |
| | CADD-5100HF | 1 | | 299 ML/24 HR | +/- 6% |
| | CADD-5100HFX | 1 | | 299 ML/24 HR | +/- 6% |
| | CADD-5101HF | 1 | | 299 ML/24 HR | +/- 6% |
| | CADD-5200 | 1 | | 19.9 MG/HR;1.0 MG/ML CONC | +/- 6% |
| | CADD-5200P | 1 | | 19.9 MG/HR;1.0 MG/ML CONC | +/- 6% |
| | CADD-5200PXC | 1 | | 19.9 MG/HR;1.0 MG/ML CONC | +/- 6% |
| | CADD-5400 | 1 | | 75 ML/HR | +/- 6% |
| | CADD-5700 | 1 | | 250 ML/HR | +/- 8% |
| | CADD-5800 | 1 | | 20 ML/HR | +/- 6% |
| | CADD-5800P | 1 | | 20 ML/HR | +/- 6% |
| SABRATEK | 3030 | 1 | | 300 ML/HR | +/- 5% |

| NO. OF OCCLUSION TESTS PER CHANNEL | OCCLUSION TEST DESIGNATOR | OCCLUSION FLOW RATE | OCCLUSION PRESSURE SPEC. | MINIMUM AIR BUBBLE SIZE | AIR DETECTION TEST DESIGNATOR | ELECTRICAL SAFETY | PM INTERVAL |
|---|---|---|---|---|---|---|---|
| 1 | CK LINE | 180 CC/HR | < 45 PSIG | 50 MICROLITERS | AIR | NO | |
| 1 | CK LINE | 180 CC/HR | < 45 PSIG | 50 MICROLITERS | AIR | NO | |
| 1 | CK LINE | 60 CC/HR | < 45 PSIG | 50 MICROLITERS | CK LINE | NO | |
| 1 | CK LINE | 60 CC/HR | < 45 PSIG | 50 MICROLITERS | CK LINE | NO | |
| 1 | CK LINE | 180 CC/HR | < 45 PSIG | 50 MICROLITERS | CK LINE | NO | |
| 1 | CK LINE | 180 CC/HR | < 45 PSIG | 50 MICROLITERS | AIR | NO | |
| 1 | OCCLUSION | 60 CC/HR | < 45 PSIG | 50 MICROLITERS | AIR IN LINE * A | NO | |
| 1 | OCCLUSION | 60 CC/HR | < 45 PSIG | 50 MICROLITERS | AIR IN LINE * B | NO | |
| 1 | OCCLUSION | 25 ML/HR | < 45 PSIG | 50 MICROLITERS | AIR IN LINE | NO | |
| N/A | | | | | | NO | |
| 1 | HI P ALARM | | N/A | N/A | | NO | |
| 1 | HI P ALARM | | N/A | N/A | | NO | |
| 1 | HI P ALARM | | N/A | N/A | | NO | |
| N/A | | | | | | NO | |
| 1 | HI P ALARM | | N/A | N/A | | NO | |
| 1 | HI P ALARM | | N/A | N/A | | NO | |
| 1 | HI P ALARM | | N/A | N/A | | NO | |
| 1 | HI P ALARM | | N/A | N/A | | NO | |
| 1 | HI P ALARM | | N/A | N/A | | NO | |
| 2 | DOWN OCCLUSION | 125 ML/HR | 100 MICROLITERS | 100 MICROLITERS | AIR IN LINE | YES | 6 MOS. |
| | DOWN OCCLUSION | | | | | | |

FIG. 13

| 1 | UNIT CLEAN |
|---|---|
| 2 | LOOSE COMPONENT (VIBRATION) CHECK |
| 3 | POWER CORD INSPECTION |
| 4 | KEYPAD & DISPLAY WINDOW (VISUAL CHECK) |
| 5 | CASE ASSEMBLY |
| 6 | DOOR ASSEMBLY |
| 7 | PUMP MEMBRANE |
| 8 | POLE CLAMP |
| 9 | POWER UP ON AC POWER |
| 10 | POWER UP ON BATTERY POWER |
| 11 | KEYPAD FUNCTIONALITY |
| 12 | BOLUS BUTTON FUNCTIONALITY |
| 13 | AIR IN LINE DETECTOR |
| 14 | EMPTY DETECTION |
| 15 | PROPER LABELS |
| 16 | FINAL VISUAL INSPECTION |
| 17 | DOCUMENTATION COMPLETE |
| 18 | BATTERY DOOR INSPECTION |
| 19 | LATCH ASSEMBLY INSPECTION |
| 20 | POWER UP ON EXTERNAL BATTERY |
| 21 | PRIME BUTTON FUNCTIONALITY |
| 22 | MEMORY CHECK |
| 23 | REMOTE BOLUS CORD FUNCTIONALITY |
| 24 | FLOW (DROP) SENSOR |
| 25 | AUDIBLE ALARM VOLUME CONTROL |
|  | ACCURACY TEST - CHANNEL 1 |
| 26 | UPSTREAM OCCLUSION - CH 1 |
| 27 | DOWNSTREAM OCCLUSION TEST CH 1 - LEVEL |
| 28 | DOWNSTREAM OCCLUSION TEST CH 1 - LEVEL |
| 29 | DOWNSTREAM OCCLUSION TEST CH 1 - LEVEL |
|  | ACCURACY TEST - CHANNEL 2 |
| 26 | UPSTREAM OCCLUSION  CH 2 CH 1-LEVEL |
| 27 | ACCURACY TEST - CHANNEL 2 |
| 28 | DOWNSTREAM OCCLUSION TEST CH 2-LEVEL |
| 29 | DOWNSTREAM OCCLUSION TEST CH 2-LEVEL |
| 30 | ELECTRICAL SAFETY |
| 31 | BATTERY LIFE |

| # | Test | Provider One | Provider One+ | Provider 2000+ | Provider 4000+ | Provider 5000 | Provider 5500 | Provider 6000 | Pain Management Provider | CADD-5100 | CADD-5100HF | CADD-5100HFX | CADD-5101HF | CADD-5200 | CADD-5200P | CADD-5200PXC | CADD-5400 | CADD-5700 | CADD-5800 | CADD-5800P | 3030 |
|---|---|---|---|---|---|---|---|---|---|---|---|---|---|---|---|---|---|---|---|---|---|
| | Manufacturer | Abbott Laboratories | | | | | | | | Pharmacia Deltec | | | | | | | | | | | Sabratek |
| 1 | UNIT CLEAN | X | X | X | X | X | X | X | X | X | X | X | X | X | X | X | X | X | X | X | X |
| 2 | LOOSE COMPONENT (VIBRATION) CHECK | X | X | X | X | X | X | X | X | X | X | X | X | X | X | X | X | X | X | X | X |
| 3 | POWER CORD INSPECTION | | | | | | | | | | | | | | | | | | | | |
| 4 | KEYPAD & DISPLAY WINDOW (VISUAL CHECK) | X | X | X | X | X | X | X | X | X | X | X | X | X | X | X | X | X | X | X | X |
| 5 | CASE ASSEMBLY | X | X | X | X | X | X | X | X | X | X | X | X | X | X | X | X | X | X | X | X |
| 6 | DOOR ASSEMBLY | | | | | | | | | | | | | | | | | | | | X |
| 7 | PUMP MEMBRANE | | | | | | | | | | | | | | | | | | | | |
| 8 | POLE CLAMP | | | | | | | | | | | | | | | | | | | | X |
| 9 | POWER UP ON AC POWER | | | | | | | | X | | | | | | | | | | | | X |
| 10 | POWER UP ON BATTERY POWER | X | X | X | X | X | X | X | X | X | X | X | X | X | X | X | X | X | X | X | X |
| 11 | KEYPAD FUNCTIONALITY | X | X | X | X | X | X | X | X | X | X | X | X | X | X | X | X | X | X | X | X |
| 12 | BOLUS BUTTON FUNCTIONALITY | | | | X | X | X | X | X | | | | X | X | X | | | X | X | | |
| 13 | AIR IN LINE DETECTOR | X | X | X | X | X | X | X | X | | | | | | | | | | | | X |
| 14 | EMPTY DETECTION | | | | | | | | | | | | | | | | | | | | |
| 15 | PROPER LABELS | X | X | X | X | X | X | X | X | X | X | X | X | X | X | X | X | X | X | X | X |
| 16 | FINAL VISUAL INSPECTION | X | X | X | X | X | X | X | X | X | X | X | X | X | X | X | X | X | X | X | X |
| 17 | DOCUMENTATION COMPLETE | X | X | X | X | X | X | X | X | X | X | X | X | X | X | X | X | X | X | X | X |
| 18 | BATTERY DOOR INSPECTION | X | X | X | X | X | X | X | X | X | X | X | X | X | X | X | X | X | X | | X |
| 19 | LATCH ASSEMBLY INSPECTION | X | X | X | X | X | X | X | X | | | | | | | | | | | | |
| 20 | POWER UP ON EXTERNAL BATTERY | X | X | | | | | | | | | | | | | | | | | | |
| 21 | PRIME BUTTON FUNCTIONALITY | X | X | X | X | X | X | X | X | X | X | X | X | X | X | X | X | X | X | X | |
| 22 | MEMORY CHECK | X | X | X | X | X | X | X | X | | | | | | | | | | | | |
| 23 | REMOTE BOLUS CORD FUNCTIONALITY | | | | X | X | X | | | | | | | | | | | | X | | |
| 24 | FLOW (DROP) SENSOR | | | | | | | | | | | | | | | | | | | | X |
| 25 | AUDIBLE ALARM VOLUME CONTROL | | | | | | | | | | | | | | | | | | | | X |
| | ACCURACY TEST - CHANNEL 1 | | X | X | X | X | X | X | X | X | X | X | X | X | X | X | X | X | X | X | X |
| 26 | UPSTREAM OCCLUSION - CH 1 | | | | | | | | | | | | | | | | | | | | |
| 27 | DOWNSTREAM OCCLUSION TEST CH 1 | X | X | X | X | X | X | X | X | X | X | X | X | X | X | X | X | X | X | X | X |
| 28 | DOWNSTREAM OCCLUSION TEST CH 1 | | | | | | | | | | | | | | | | | | | | |
| 29 | DOWNSTREAM OCCLUSION TEST CH 1 | | | | | | | | | | | | | | | | | | | | |
| | ACCURACY TEST - CHANNEL 2 | | | | | X | | | | | | | | | | | | | | | |
| 26 | UPSTREAM OCCLUSION - CH 2 | | | | | | | | | | | | | | | | | | | | |
| 27 | DOWNSTREAM OCCLUSION TEST CH 2 | | | | | X | | | | | | | | | | | | | | | |
| 28 | DOWNSTREAM OCCLUSION TEST CH 2 | | | | | | | | | | | | | | | | | | | | |
| 29 | DOWNSTREAM OCCLUSION TEST CH 2 | | | | | | | | | | | | | | | | | | | | |
| 30 | ELECTRICAL SAFETY | | | | | | | | | | | | | | | | | | | | |
| 31 | BATTERY LIFE | | | | | | | | | | | | | | | | | | | | |

| MANUFACTURER | MODEL | ACCURACY FLOW RATE | FLOW RATE ACCURACY SPEC. | OCCLUSION FLOW RATE | OCCLUSION PRESSURE SPEC. |
|---|---|---|---|---|---|
| ABBOTT LABORATORIES | PROVIDER ONE | 250 CC/HR | +/- 5% | 180 CC/HR | 45 PSIG |
| | PROVIDER ONE + | 250 CC/HR | +/- 5% | 180 CC/HR | 45 PSIG |
| | PROVIDER 2000+ | | +/- 5% | 60 CC/HR | 45 PSIG |
| | PROVIDER 4000+ | | +/- 5% | 60 CC/HR | 45 PSIG |
| | PROVIDER 5000 | 240 CC/HR | +/- 5% | 180 CC/HR | 45 PSIG |
| | PROVIDER 5500 | 240 CC/HR | +/- 5% | 180 CC/HR | 45 PSIG |
| | PROVIDER 6000 | 240 CC/HR | +/- 5% | 60 CC/HR | 45 PSIG |
| | | 240 CC/HR | +/- 5% | 25 CC/HR | 45 PSIG |
| PHARMACIA DELTEC | PAIN MANAGEMENT PROVIDER | 125 ML/HR | +/- 6% | | |
| | CADD-5100 | 299 ML/24 HR | +/- 6% | | 16 TO 40 PSI |
| | CADD-5100HF | 299 ML/24 HR | +/- 6% | | 16 TO 40 PSI |
| | CADD-5100HFX | 299 ML/24 HR | +/- 6% | | 16 TO 40 PSI |
| | CADD-5101HF | 299 ML/24 HR | +/- 6% | | |
| | CADD-5200 | 19.9 MG/HR;1.0 MG/ML CONC | +/- 6% | | 16 TO 40 PSI |
| | CADD-5200P | 19.9 MG/HR;1.0 MG/ML CONC | +/- 6% | | 16 TO 40 PSI |
| | CADD-5200PXC | 19.9 MG/HR;1.0 MG/ML CONC | +/- 6% | | 16 TO 40 PSI |
| | CADD-5400 | 75 ML/HR | +/- 6% | | 16 TO 40 PSI |
| | CADD-5700 | 250 ML/HR | +/- 8% | | 10 TO 34 PSI |
| | CADD-5800 | 20 ML/HR | +/- 6% | | 16 TO 40 PSI |
| | CADD-5800P | 20 ML/HR | +/- 6% | | 16 TO 40 PSI |
| SABRATEK | 3030 | 300 ML/HR | +/- 5% | 125 ML/HR | 3 TO 13 PSI |
| | | | | | 15 TO 25 PSI |

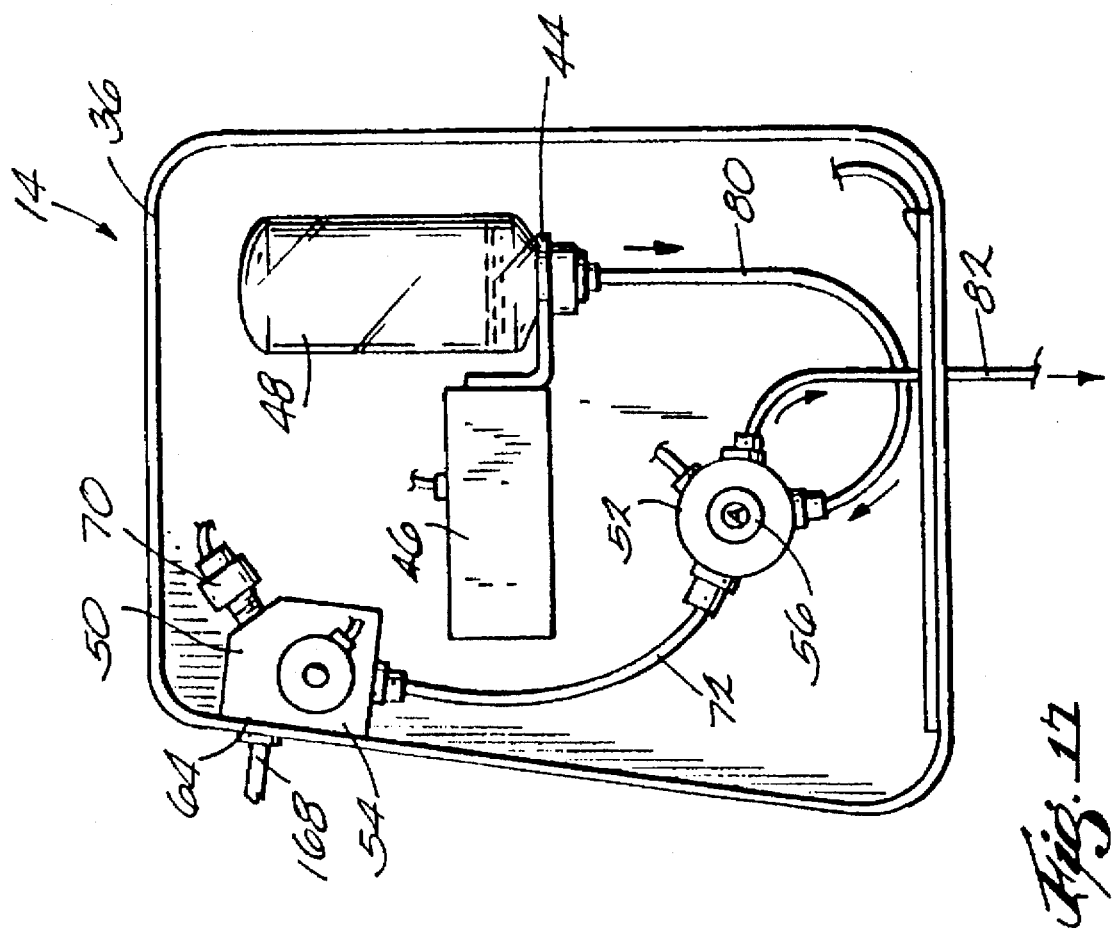

FIG. 21

PUMP CERTIFICATION REPORT

MANUFACTURER : PCI MEDICAL
MODEL : AC PUMP
SERIAL NUMBER : 335
DATE : August 3, 1994

The above listed device has been tested and found to meet all the current manufacturer's specifications for performance and safety. The tests that were completed are listed on the following pages.

Sam Jones, Operator

| PUMP CERTIFICATION | |
|---|---|
| TESTED | 08/03/94 |
| CERTIFIED | 08/03/94 |

PUMP FAILURE REPORT

MANUFACTURER : PCI MEDICAL
MODEL : AC PUMP
SERIAL NUMBER : 335
DATE : August 3, 1994

The above listed device has been tested and found to fail to meet one or more of the current manufacturer's specifications for performance and safety. The tests that were completed and failed are listed on the following pages.

---

Sam Jones, Operator

FIG. 23A

DETAILED TEST RESULTS

| | |
|---|---|
| MODEL NUMBER: AC PUMP | TEST DATE: August 3, 1994 |
| SERIAL NUMBER: 335 | OPERATOR: SAM JONES |

Visual Inspection Tests
   Passed  Unit Clean
   Passed  Loose Component Check
   Passed  Power Cord Inspection
   Passed  Keypad & Display Window
   Passed  Case & Door Assembly
   Passed  Pump Membrane
   Passed  Pole Clamp
   Passed  Power-Up on Battery
   Passed  Keypad Functionality
   Passed  Air In Line Detection
   Passed  Empty Detection
   Passed  Power Up On AC Power
   Passed  Documentation Complete
   Passed  Proper Labels
   Passed  Final Visual Inspection

Flow Rate Accuracy Tests
   Passed  143.9 mL/hr. Channel 0 Flow Accuracy Test
   Passed  152.0 mL/hr. Channel 1 Flow Accuracy Test

Occlusion Tests
   FAILED  Downstream Occlusion Test Level 0
   FAILED  Downstream Occlusion Test Level 1
   Passed  Upstream Occlusion Test

Electrical Safety Tests
   FAILED  Internal Leakage; AC Off, Reverse Polarity, No Ground: 125uA
   Passed  Internal Leakage; AC Off, Reverse Polarity, With Ground: 51 uA
   Passed  Internal Leakage; AC On, Reverse Polarity, No Ground: 54 uA
   FAILED  Internal Leakage; AC On, Reverse Polarity, With Ground : 141uA
   FAILED  Internal Leakage; AC Off, Normal Polarity, No Ground : 116 uA
   Passed  Internal Leakage; AC Off, Normal Polarity, With Ground : 68 uA
   Passed  Internal Leakage; AC On, Normal Polarity, No Ground : 54 uA
   Passed  Internal Leakage; AC On, Normal Polarity, No Ground : 54 uA
   Passed  External Leakage; AC Off, Reverse Polarity, No Ground : 54 uA
   FAILED  External Leakage; AC Off, Reverse Polarity, With Ground : 142 uA
   FAILED  External Leakage; AC On, Reverse Polarity, No Ground : 140 uA
   Passed  External Leakage; AC On, Reverse Polarity, With Ground : 53 uA
   FAILED  External Leakage; AC Off, Normal Polarity, With Ground : 53 uA
   FAILED  External Leakage; AC Off, Normal Polarity, With Ground : 102 uA
   Passed  External Leakage; AC On, Normal Polarity, No Ground : 79 uA
   Passed  External Leakage; AC On, Normal Polarity, With Ground : 85 uA
   FAILED  Ground Wire Resistance 1.24 Ohms

FIG. 23B

FLOW RATE ACCURACY DATA
CHANNEL OF FLOW ACCURACY TEST

MODEL: AC PUMP
SERIAL NUMBER: 335
TEST DATE: AUGUST 3, 1994
PROGRAMMED FLOW RATE: 150.0 ML/HR
ACCEPTABLE % ERROR: 5%
NUMBER OF CONSECUTIVE SAMPLES: 10

| SAMPLE # | INTERNAL FLOW RATE (mL/HR) | INTERNAL FLOW RATE % ERROR | INTERVAL DELIVERED VOLUME (mL) | AVERAGE FLOW RATE (mL/HR) | AVERAGE FLOW RATE % ERROR | CUMULATIVE DELIVERED VOLUME mL |
|---|---|---|---|---|---|---|
| 1 | 149.9 | -0.1 | 2.50 | 149.9 | -0.1 | 2.50 |
| 2 | 141.3 | -5.8 | 2.36 | 145.6 | -2.9 | 4.85 |
| 3 | 144.7 | -3.6 | 2.41 | 145.3 | -3.1 | 7.26 |
| 4 | 148.6 | -0.9 | 2.48 | 146.1 | -2.6 | 9.74 |
| 5 | 157.5 | 5.0 | 2.62 | 148.4 | -1.1 | 12.36 |
| 6 | 150.0 | -0.0 | 2.50 | 148.6 | -0.9 | 14.86 |
| 7 | 145.9 | -2.8 | 2.43 | 148.2 | -1.2 | 17.30 |
| 8 | 146.3 | -2.5 | 2.44 | 148.0 | -1.3 | 19.73 |
| 9 | 159.2 | 6.1 | 2.65 | 149.2 | -0.5 | 22.39 |
| 10 | 143.9 | -4.0 | 2.40 | 148.7 | -0.9 | 24.79 |

FLOW RATE ACCURACY TEST IF FAILED
TESTED BY: SAM JONES
SAMPLE INTERVAL: 1 MINUTE

FIG. 23C

Flow Rate Accuracy Data
Channel 1 Flow Accuracy Test

Model: AC PUMP
Serial Number: 335
Test Date: August 3, 1994
Programmed Flow Rate: 150.0 mL/hr
Acceptable % Error: 5%
Number of Consecutive Samples: 10
Sample Interval: 1 Minute

| SAMPLE # | INTERNAL FLOW RATE (mL/HR) | INTERNAL FLOW RATE % ERROR | INTERVAL DELIVERED VOLUME (mL) | AVERAGE FLOW RATE (mL/HR) | AVERAGE FLOW ATE % ERROR | CUMULATIVE DELIVERED VOLUME mL |
|---|---|---|---|---|---|---|
| 1 | 151.6 | 1.1 | 2.53 | 151.6 | 1.1 | 2.53 |
| 2 | 159.5 | 6.3 | 2.66 | 155.6 | 3.7 | 5.19 |
| 3 | 153.8 | 2.6 | 2.56 | 155.0 | 3.3 | 7.75 |
| 4 | 145.6 | -2.9 | 2.43 | 152.7 | 1.8 | 10.18 |
| 5 | 146.6 | -2.2 | 2.44 | 151.5 | 1.0 | 12.62 |
| 6 | 157.5 | 5.0 | 2.63 | 152.5 | 1.6 | 15.25 |
| 7 | 142.1 | -5.2 | 2.37 | 151.0 | 0.7 | 17.61 |
| 8 | 156.1 | 4.1 | 2.60 | 151.6 | 1.1 | 20.22 |
| 9 | 142.3 | -5.1 | 2.37 | 150.6 | 0.4 | 22.59 |
| 10 | 152.0 | 1.3 | 2.53 | 150.7 | 0.5 | 25.12 |

FLOW RATE ACCURACY TEST IF FAILED
TESTED BY: SAM JONES

Fig. 14A

| Unit Clean | | |
|---|---|---|
| ☐ Fail | Detail | ☒ Pass |

| Loose Component Check | | |
|---|---|---|
| ☐ Fail | Detail | ☒ Pass |

| Power Cord Inspection | | |
|---|---|---|
| ☐ Fail | Detail | ☒ Pass |

| Keypad & Display Window | | |
|---|---|---|
| ☐ Fail | Detail | ☒ Pass |

| Case & Door Assembly | | |
|---|---|---|
| ☐ Fail | Detail | ☒ Pass |

| Pump Membrane | | |
|---|---|---|
| ☐ Fail | Detail | ☒ Pass |

| Pole Clamp | | |
|---|---|---|
| ☐ Fail | Detail | ☒ Pass |

| Power-Up on Battery | | |
|---|---|---|
| ☐ Fail | Detail | ☒ Pass |

| Keypad Functionality | | |
|---|---|---|
| ☐ Fail | Detail | ☒ Pass |

| Help | | |
|---|---|---|

| Time Remaining<br>4:54 | Occlusion Alarm<br>Audible/Visual<br>Signal Functionality<br>☐ Fail  ☒ Pass |
|---|---|
| PASSED | |

Fig. 27

| | Visual Inspection | ✓ |
| | Flow Rate Accuracy | ✓ |
| × | Occlusion Pressure | |
| × | Electrical Safety | |

| Passed | | Preview | Print | Done |

INTEGRATED TEST STATION FOR TESTING LIQUID FLOW AND ELECTRICAL SAFETY CHARACTERISTICS OF IV PUMPS

This is a continuation of application Ser. No. 08/293,238 filed on Aug. 19, 1994 now abandoned.

FIELD OF THE INVENTION

The invention relates to systems and methods for testing the physical, functional, and electrical performance of pumps.

BACKGROUND OF THE INVENTION

There are many types and styles of pumps intended to administer liquids, medications, and solutions intravenously. Such pumps (commonly called "IV pumps") operate in various ways; for example, by syringe, diaphragm, peristaltic, and fluid pressure action.

Because of their intended use, IV pumps must meet stringent requirements for accuracy and safety. IV pumps also require periodic certification of their physical, functional, and electrical performance characteristics.

Today, testing and certification of IV pumps are typically performed by facilities with trained technical staffs. The pump owner loses use of the pump during shipment of the pump to the test facility, and while the pump facility performs its services and ships the pump back.

There is a need for a system that a non-technical person can conveniently use to test and completely certify IV pump performance on site, without assistance of often distant test facilities.

SUMMARY OF THE INVENTION

The invention provides a pump testing apparatus that makes possible the integration of liquid flow testing with the testing of electrical characteristics of an IV pump.

The testing apparatus that embodies the features of the invention includes a housing having an interior. A first component in the housing is adapted to be coupled in liquid flow communication with an external intravenous pump to test at least one liquid flow characteristic of the pump. A second component in the housing is adapted to be coupled electrically to the pump to test at least one electrical characteristic of the pump. According to the invention, an interior panel compartmentalizes the housing into two compartments isolated one from the other. The first component is confined solely within one of the compartments and the second component is confined solely within the other one of the compartments.

The interior panel creates a dry chamber and a wet chamber within the same housing. The panel shields the electrical components in the dry chamber from exposure to liquid handled in the wet chamber. The panel thereby isolates within the housing all high voltage electrical components from all liquid handling components.

In a preferred embodiment, a controller in the compartment housing the electrical component generates control signals to operate the first component and the second component. The controller itself preferably operates in response to control signals received from an external host processor.

Other features and advantages of the inventions are set forth in the following specification and attached drawings.

BRIEF DESCRIPTION OF THE DRAWINGS

FIG. 1 is a perspective view of an integrated system for testing and certifying the physical, functional and electrical performance of IV pumps, which embodies the features of the invention;

FIG. 2 is a perspective view of the system shown in FIG. 1 configured as a testing and certifying network simultaneously serving multiple test stations;

FIG. 3 is a front right perspective view of the test station associated with the system shown in FIG. 1;

FIG. 4 is a right side elevation view of the testing station shown in FIG. 3, showing the interior of the wet chamber, where liquid conveyance testing is accomplished;

FIG. 6B is a schematic view of the first circuit board housed within the dry chamber, which carries the components for testing the electrical safety of an IV pump;

FIG. 6C is a schematic view of the second circuit board housed within the dry chamber, which carries a microprocessor and other components for controlling liquid flow and electrical tests upon an IV pump;

FIG. 7 is a front section view of the integral valve block that serves as the inlet valve station for the wet chamber of the testing station;

FIG. 8 is side section view of the integral valve block shown in FIG. 7, taken generally along lines 8—8 in FIG. 7;

FIG. 9 is a top view of the liquid detection pad housed within the wet chamber of the testing station;

FIG. 10 is a schematic block view of the principal elements comprising the host processing station, the test station, and the data reporting station of the system shown in FIG. 1;

FIG. 11C is a schematic flow chart view showing the operation of the host program in generating reports;

FIGS. 12A–12B, collectively referred to hereinafter as FIG. 12 are a representative excerpt of the Pump Specification Database that forms a part of the host CPU;

FIG. 13 is a representative Master Test Listing Database that forms a part of the host CPU;

FIGS. 14A–14C are representative Test Matrixes that the host program generates based upon correlating the Pump Specification Database and the Master Test Listing Database;

FIG. 17 is a side elevation view of the wet chamber of the test station, largely in schematic form, during the draining of the test station after performance of the liquid conveyance tests;

FIG. 21 is a representative Pump Certification Report generated by the host program based upon information containing in the log file database;

FIG. 23A is a representative Detailed Test Result Report generated by the host program based upon information containing in the log file database, detailing the tests conducted and the results;

FIG. 23B is a representative Detailed Test Result Report generated by the host program based upon information containing in the log file database, detailing the data collected during the flow rate accuracy tests for a two channel pump;

FIG. 24A is a visual test menu used in a preferred implementation of the host program;

FIG. 24B is a help screen for the visual test menu shown in FIG. 24A, used in a preferred implementation of the host program;

FIG. 27 is a visual display of the test results score card used in a preferred implementation of the host program;

Figure 6A:
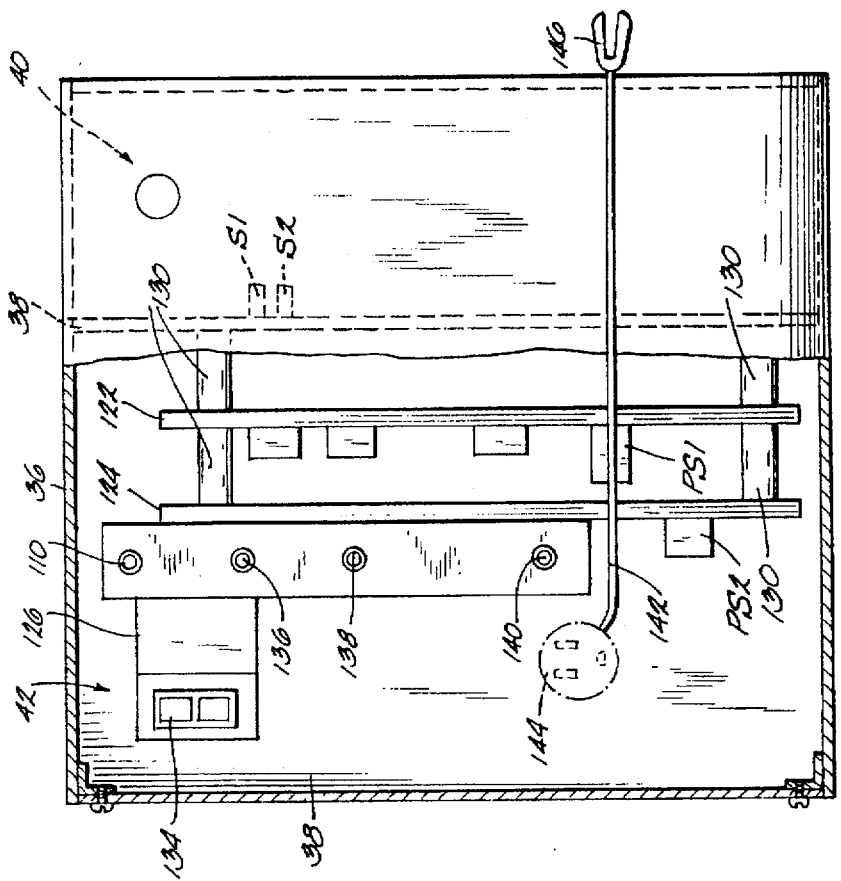
FIG. 6A is a front elevation view of the testing station, with the front panel broken away in sections to further show the interior of the dry chamber where electrical safety testing is accomplished.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows an integrated system 10 for testing and certifying the physical, functional and electrical performance of pumps intended to administer liquids, medications, and solutions intravenously. Such pumps (commonly called "IV pumps") operate in various ways; for example, by syringe, diaphragm, peristaltic, and fluid pressure action. Because of their intended use, IV pumps must meet stringent requirements for accuracy and safety. IV pumps also require periodic certification of their physical, functional, and electrical performance characteristics. The system 10 serves just such a purpose.

The system 10 includes a host processing station 12, a test station 14, and a data reporting station 16.

As FIG. 1 shows, the stations 12, 14, and 16 are preferably arranged side-by-side as modules on a work station 18 next to the IV pump 20 that is to be tested and certified. As FIG. 1 also shows, the IV pump 20 is supported on a conventional movable stand and IV pole assembly 22.

As FIG. 1 shows, the test station 14 is adapted to be coupled electrically to the AC power cord 174 of the pump 20 (if the pump 20 is AC powered). The test station 14 carries an AC outlet plug 144 for this purpose. The test station 14 also includes a ground probe 142 that, in use, is coupled to a suitable ground connection on the pump 20.

As FIG. 1 also shows, the test station 14 is adapted to be connected in liquid flow communication with the disposable fluid administration set 168 of the IV pump 20. The test station 14 carries a female luer connector 64 for this purpose, which mates with a conventional male luer commonly carried on the distal end of fluid administration sets 168.

The host processing station 12 includes a central microprocessing unit (CPU) 24. The CPU 24 is linked to the test station 14 by a conventional serial connection cable 32 (using, for example, a conventional RS-232 interface).

The host processing station 12 also includes an interactive interface 154 for the operator. The interface 154 includes a display screen 26 (for example, a graphics display monitor or CRT), keyboard 28, and a mouse 30.

Figure 14B:
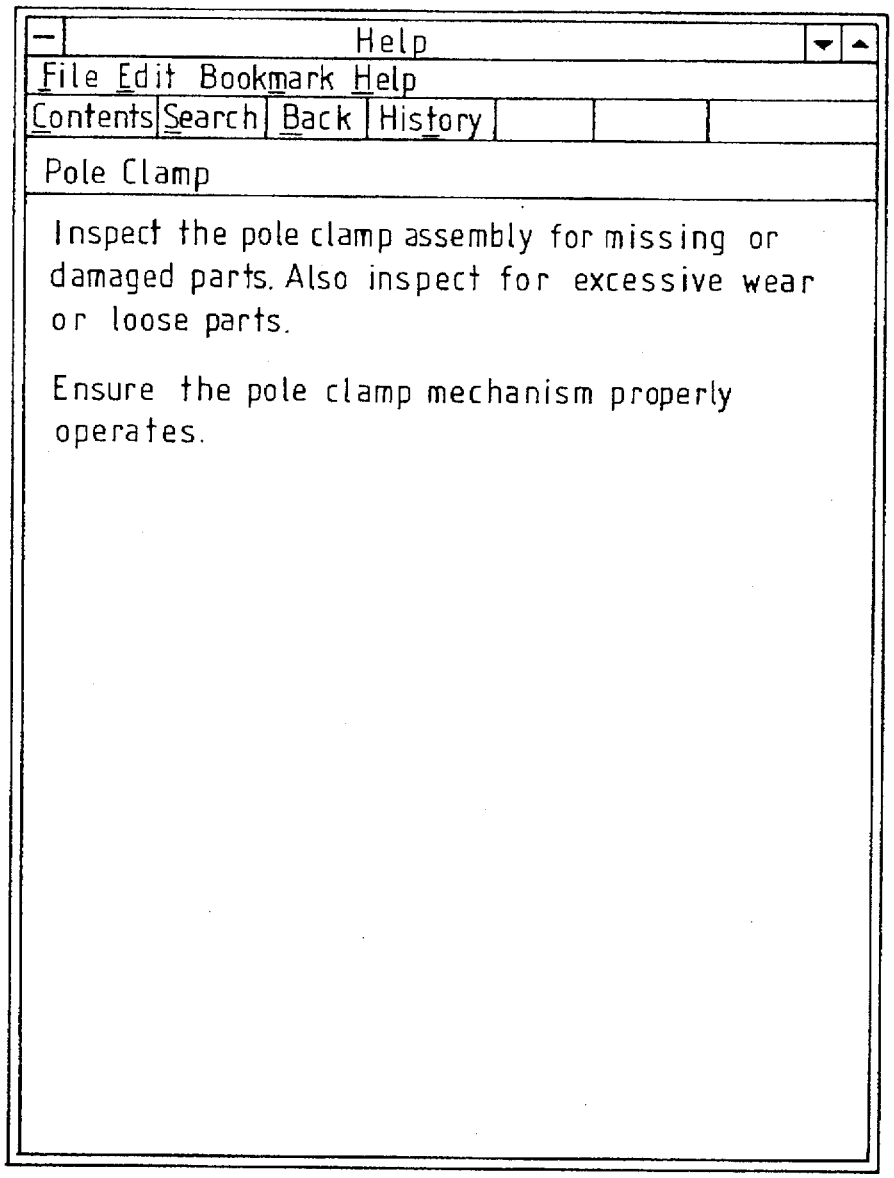

As will be described in greater detail later, the host CPU 24 executes a resident host program 160 (see FIGS. 10 and 11A/B/C). Through the host program 160, the CPU 24 generates and then implements an integrated test and certification procedure (which will also be referred to as a test matrix 162, as FIGS. 14A/B show). The host program 160 preferably customizes the test matrix 162 according to specifications of the particular IV pump that is tested. For this purpose, the host CPU 24 retains pump specifications in an onboard specification database 156 (see FIG. 12). The test matrix 162 integrates a battery of visual physical tests, liquid flow and pressure tests, and electrical safety tests for the pump 20 into one consolidated test and certification procedure.

In the illustrated and preferred embodiment, the integrated test and certification procedure includes a series of physical inspection tests performed on the pump 20 by the operator under the prompting and control of the host program 160. The integrated test and certification procedure also includes a series of flow rate accuracy tests, occlusion pressure tests, and (for AC powered pumps) electrical safety tests performed on the pump 20 by the test station 14 under the control of the host CPU 24 with assistance from the operator, when prompted by the host program 160.

In the illustrated and preferred embodiment (as will also be described later in greater detail), the host program 160 uses a graphical interface to display test status information and operator prompts on the display screen 26 as the test procedure progresses. The host interface allows the operator to interact by entering commands and responding to interface prompts, using the keyboard 28 or mouse 30. In this way, the host program leads the operator in a logical, stepwise fashion through the integrated test and certification procedure.

The automated and user-friendly nature of the interface makes possible the use of the system 10 by non-technical people to perform testing and recertification of IV pumps on site at pump distribution centers and hospitals. The system 10 eliminates the need to send IV pumps to specialized bio-medical facilities for certification. In this way, the system 10 avoids lost time and expense due to shipping, staging time at the certification facility, and returning the certified pumps to inventory.

In the illustrated and preferred embodiment (as will be described later in greater detail), the host CPU 24 also retains a log file database 164 for each IV pump tested (see FIG. 11B). The log file database 164 identifies each pump tested by make, model, and an unique alpha-numeric designation. The log file database 164 holds the historical results of each test and certification procedure conducted for each individual IV pump. The log file database 164 provides full documentation for generating a diverse number of performance and tests reports for management, certification, and failure diagnosis purposes.

A conventional parallel or serial connection cable 34 links the data reporting station 16 to the host CPU 24. In the illustrated and preferred embodiment (as FIG. 1 shows), the reporting station 16 is a dot matrix or laser printer. The host program 160 draws from the log file database 164 to transmit to the printer 16 the processed test and certification results. The printer 16 prints these reports in easily understood, preformatted reports (see FIGS. 22 to 23). As FIG. 2 shows, the host processing station 12 preferable employs conventional real-time multi-tasking. This allows the host processing station 12 to allocate CPU cycles to different application tasks and simultaneously control multiple test stations 14 in a test and calibration network 11.

The illustrated embodiment in FIG. 2 shows, by way of example, the host processing station 12 simultaneously controlling up to four test stations, designated 14(1); 14(2); 14(3); and 14(4), each associated with an individual IV pump, respectively designated 20(1); 20(2); 20(3); and 20(4). Of course, the host processing station 12 could be conditioned to simultaneously control more test stations 14, if desired.

The principal components of the system 10 will now be individually discussed in greater detail.

I. THE TEST STATION

As FIG. 3 best shows, the test station 14 includes a compact housing 36, which can be made from formed metal or molded plastic material. The test station 14 integrates within the housing 36 the testing of both electrical safety and liquid conveyance characteristics of the IV pump 20.

More particularly, the test station 14 physically isolates these two very different test functions by internally compartmentalizing the housing by a dividing plate 38. The dividing plate 38 creates two side-by-side chambers 40 and 42 within the test station 14.

One chamber 40 occupies the right front side of the housing 36. This chamber 40 (also shown in side view in FIG. 4) is dedicated to the handling of liquid conveyed by the IV pump 20. In the illustrated and preferred embodiment shown in FIG. 4, this chamber 40 holds the components that perform liquid flow rate and liquid pressure occlusion tests on IV pumps. For this reason, the chamber 40 will also be called the "wet chamber."

The other chamber 42 occupies the left front side of the housing 36. This chamber 42 (also shown in front and side views in FIGS. 5 and 6) is dedicated to the handling of high voltage electrical flow to and from AC power IV pumps 20. In the illustrated and preferred embodiment shown in FIGS. 5 and 6, this chamber 42 holds components for handling electrical output to perform a range of electrical safety tests for AC power IV pumps. For this reason, the chamber 42 will be also called the "dry chamber."

The dividing plate 38 shields the electrical components in the dry chamber 42 from exposure to liquid handled in the wet chamber 40. The dividing plate 38 thereby isolates within the test station housing 36 all high voltage electrical components from all liquid handling components.

A. The Wet Chamber

The wet chamber 40 (see FIG. 4) contains a conventional load cell 44 housed within a bracket 46 mounted to the dividing plate 38. A representative load cell 44 that can be used for this purpose is manufactured by HBM Incorporated, Marlboro, Mass. (Model No. LPX-2XX109).

The load cell 44 supports a liquid collection bottle 48. Preferably, the interior volume of the bottle 48 is sufficiently large to collect liquid during flow accuracy measurements without filling. For most test purposes, a bottle 48 with a volume of about 250 cc should be adequate. Still, as will be described in greater detail later, the test station 14 can be operated to drain the bottle 48, if required, during a given test procedure, and the test procedure resumed with an emptied bottle 48.

The wet chamber 40 also contains an inlet valve station 50 and a drain valve station 52 mounted to the dividing plate 38. First and second solenoids 54 and 56 are, in turn, carried by the valve stations 50 and 52. Under the direction of the host program, the host CPU 24 independently operates the solenoids 54 and 54 to control fluid flow through the respective valve stations 50 and 52 to carry out flow accuracy and occlusion pressure tests.

The inlet valve station 50 is configured as a two way valve and includes three branches 58, 60, and 62. The first branch 58 communicates with the female luer 64 mounted on the front panel 66 of the test station housing 36. A male luer (not shown) carried at the distal end of the IV pump tubing 168 makes an interference fit within the female luer 64 to connect the pump tubing 168 to the valve station 50. The inlet valve station 50 is therefore directly subject to pumping pressure applied by the associated IV pump.

The second branch 60 of the inlet valve station 50 communicates with a conventional pressure transducer 70, which is also carried within the wet chamber 40. The third branch 62 of the inlet valve station 50 communicates with a first length 72 of flexible tubing extending within the wet chamber 40. The flexible tubing 72 is preferably made of an inert flexible plastic material, like plasticized polyvinylchloride.

The first solenoid 54 controls the pressurized fluid flow through the inlet valve station 50, under the direction of the host program, from the female luer 64 (via the first branch 58) either to the pressure transducer 70 (via the second branch 56) or to the first tubing 72 (via the third branch 62). The first solenoid 54 is normally spring biased to open liquid flow between the first branch 58 (from the female luer 64), the second branch 56 (to the pressure transducer 70), and the third branch 62 (to the first tubing 72). In this condition, pressurized liquid flows, following the path of least resistance, through the inlet valve station 50 from the female luer 64 to the drain valve station 52.

The first solenoid 56 can be activated, under the control of the host program independent of activation of the second solenoid 56, to close liquid flow between the first branch 58 (from the female luer 64) and the third branch 62 (to the first tubing 72, leading to the drain valve station 52). This condition channels all pressurized liquid flow from the first branch 58 into the second branch 60. The resulting increase in pressure in the second branch 60 is detected by the pressure transducer 70.

A representative commercially available solenoid that can serve as the first solenoid 54 is made of NR Research Inc., Northboro, Mass. (Model Number HP225T021).

The drain valve station 52 is configured as a three way valve and also includes first, second, and third branches 74, 76, and 78. The first branch 74 communicates with the first tubing 72 leading from the inlet valve station 50. The second branch 76 communicates with a second length 80 of tubing extending within the wet chamber 40, which is also preferably plasticized polyvinylchloride plastic material. The second tubing 80 leads in an iso-radial path from the drain valve station 52 to the collection bottle 48. The third branch 78 communicates with a drain tube 82 for the wet chamber 40. The drain tube 82 exits the wet chamber 40 through an opening 84 in the bottom panel 86 of the test station housing 36. The drain tube 82 is also preferably plasticized polyvinylchloride plastic material.

A second solenoid 56 controls fluid flow through the drain valve station 52, under the direction of the host program, from the first tubing 72 (via the first branch 74) either to the collection bottle 48 (via the second branch 76 and tubing 80) or to drain tube 82 (via the third branch 78).

The second solenoid 56 is normally spring biased to open liquid flow between the first branch 74 (from the first tubing 72), and the second branch 76 (to the second tubing 80 leading to the collection bottle 48), while closing liquid flow through the third branch 78 (to the drain tube 82). In this condition, the drain valve station 52 directs liquid from the inlet valve station 50 to the collection bottle 48. By sensing with the load cell 44 the change in weight of the bottle 48 over time, and knowing the specific gravity of the liquid being conveyed, the host program 160 derives a flow rate calculation gravimetrically.

The second solenoid 56 can be activated, under the control of the host program 160, independent of activation of the first solenoid 54, to open liquid flow between the second branch 76 (from the second tubing 80 leading from the collection bottle 48) and the third branch 78 (to the drain tube 82). This allows liquid in the bottle 48 to drain by gravity pressure through the drain tube 82. If the IV pump 20 is still operating and the first solenoid 54 is not activated, pressurized liquid flowing from the inlet valve station 50 will also follow the path of least resistance through the drain tube 82.

A representative commercially available solenoid that can serve as the first solenoid is made of NR Research Inc., Northboro, Mass. (Model Number 648T031).

In the illustrated and preferred embodiment (see FIGS. 7 and 8), the inlet valve station 50 minimizes the number of high pressure, leak-prone connections by consolidating them into integral valve block 88 attached to the dividing plate 38. The valve block is made of an inert plastic material that makes leak resistant threaded connections, like Teflon plastic. The block 88 contains drilled interior passageways that comprise the first, second, and third branches 58, 60, and 62 already described. The first branch passageway 58 joins the second branch passageway 60, and together they join an orifice 90 that enters a preformed valve seat 92 on the block 88. The second branch passageway 60 joins a second orifice 94 that also enters the valve seat 92. The first solenoid 54 is mounted to the block 88 overlying the valve seat 92. In its normally biased, inactivated position, the first solenoid 54 is withdrawn from the valve seat 92. This allows liquid flow through the valve seat 92 between the orifices 90 and 92, through the first and second branch passageways 58/60 into the third branch passageway 62. When activated, the first solenoid 54 seats inside the value seat 92, blocking the orifices 90 and 92 and thereby blocking the liquid flow between them. The pressurized flow thereby collects in the second branch passageway 56 for pressure detection by the pressure transducer 70.

The first, second, and third branch passageways 58, 60, and 62 include internally threaded ports 96 that mate with threaded connectors 98 on the female luer 64, the pressure transducer 70, and the first tubing 72. Consolidated, secure, and leakproof conveyance of liquid through the valve station block 88 results.

While not shown, a similar integral block construction could be used to form the drain valve station 52, or to consolidate the inlet and drain valve stations 50 and 52 into a single valve block.

In the illustrated and preferred embodiment (see FIG. 4), the wet chamber 40 includes a liquid spill detection element 100. The element 100 detects the leakage of liquid within the wet chamber 40. The leakage, if not detected, could adversely impact the accuracy of the flow rate calculations.

The spill detection element 100 can be constructed in various ways. In the illustrated and preferred embodiment (see FIG. 9), the spill detection element 100 comprises pad 102 of electrically non-conducting material mounted on the bottom panel 86 of the wet chamber 40. Various non-conducting materials can be used. In the illustrated and preferred embodiment, the pad 102 is made of a polyester material.

First and second circuits 104 and 106 of electrically conducting material, like copper, are applied by coating or by etching or by imbedding thin wires on the pad 102 (see FIG. 9). The first and second circuits 104 and 106 form an array of spaced apart fingers 108, which are nested in an alternating pattern on the pad 102.

The first and second circuits 104 and 106 are normally insulated from each other by the pad material between the alternating fingers 108, so that the first and second circuits 104 and 106 normally conduct no current between them. The presence of one or more liquid droplets on the pad 102 spanning across the alternating fingers 108 electrically connects the first and second circuits 104 and 106 to conduct current and illuminate an LED 110 on the front panel 66 of the test station housing 36 (see FIG. 3). When illuminated, the LED 110 alerts the operator to the leakage of liquid within the wet chamber 40.

When the pad 102 senses liquid leakage, a signal is also relayed to the host CPU 24 indicating the problem. The host CPU 26 also displays a "liquid leakage" message on the screen 26 (and preferably also sounds an audible alarm) to alert the operator.

As FIGS. 3 and 4 show, the right side of the test station housing 36 includes a door 112 mounted on a piano hinge 114. The door 112 opens and closes to provide access to the wet chamber 40. A conventional magnetic release latch 116 (see FIG. 4) normally holds the access door 112 closed during use.

In the illustrated and preferred embodiment (as FIG. 4 shows), the interior of the access door 112 includes a bracket 118 that carries weights (designated W1 and W2 in FIG. 4) of predetermined size. Upon prompting by the host program 160, the operator opens the access door 112 and places one or more of the weights W1/W2 upon the collection bottle 48 to calibrate the load cell 44. The details of this calibration process governed by the host program 160 will be described later.

In a preferred embodiment, the test station housing 36 includes a conventional proximity sensor 120 (see FIG. 4) to sense when the access door 112 is opened. The host program 160 appropriately prompts the operator with an "Open Door" indication in response to a signal relayed to it from the proximity sensor 120. Upon receiving an "Open Door" signal from the sensor 120, the host CPU 24 preferably also aborts any tests involving components in the wet chamber 40. Upon closing the access door 112, the host CPU 24 restarts an aborted test from the beginning.

It should be realized that flow accuracy measurements could be accomplished in ways different than gravimetrically. For example, the wet chamber 40 could include a fixed volume capillary tube and photosensors to measure flow rates volumetrically. Because the capillary tube becomes partially or totally occluded by bacterial growth or liquid residue within it, volumetric systems are prone to inaccuracies and results that are not uniformly repeatable. For this reason, the gravimetric method for measuring flow rates is preferred.

B. The Dry Chamber

Figure 5:
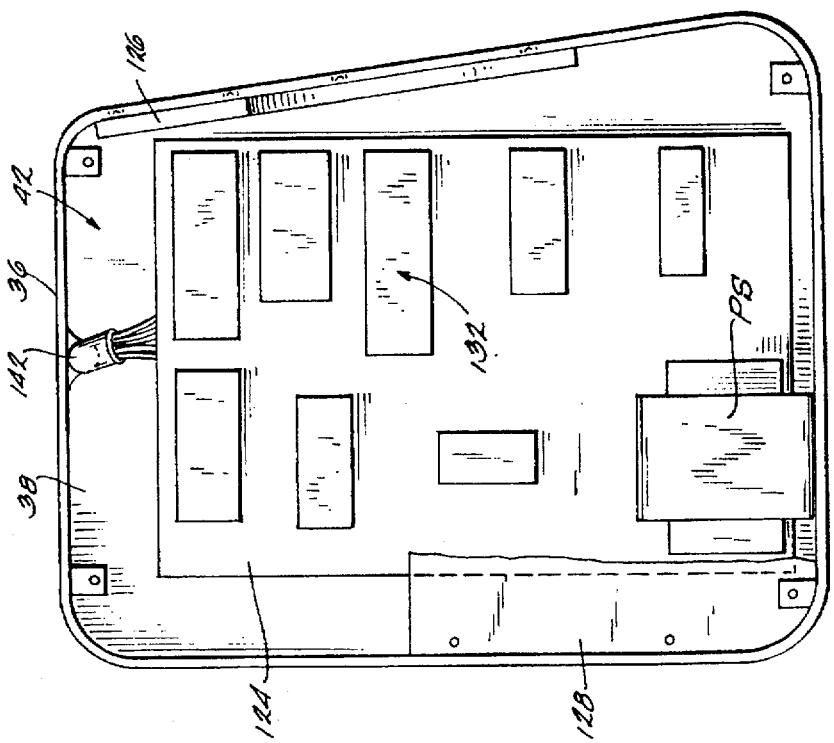
FIG. 5 is a left side elevation view of the testing station shown in FIG. 3, showing the interior of the dry chamber, where electrical safety testing is accomplished.

Please refer now to FIGS. 5 and 6A/B/C. The dry chamber 42 houses on three integrated circuit boards 122, 124, and 124 the numerous components that assist in the acquisition and processing of electrical data by the test station 14, as well as the communication of this data to the host CPU 24. A left side panel 128 closes the dry chamber 42, protecting the boards 122, 124, and 126 from direct access and exposure to the outside environment. As before stated, the dividing panel 38 protects the boards 122, 124, and 126 from unintended contact with liquid in the wet chamber 40, and vice-versa.

Spacers 130 attach the first circuit board 122 to the dividing panel 38 (see FIG. 6A). The first circuit board 122 (shown schematically in block form in FIG. 6B) carries the various relays and electrical components 68 needed to check internal and external electrical leakage in the IV pump 20 with normal and reverse polarities, with and without ground, and with and without AC power applied. Further details of the electrical components 68 and their operation will be described later.

The first circuit board 122 includes a low voltage AC (115V) power supply PS1. This power supply PS1 powers the relays and electrical components 68 on the board 122, the solenoids 50 and 52 in the wet chamber 40, and the serial port interface 188 between the host CPU 32 and the test station microprocessor 132 (mounted on the second circuit board 124).

The second circuit board 124 is attached by additional spacers 130 to the first circuit board 122 in the dry chamber 42 (see FIG. 6A). The second circuit board 124 (shown schematically in block form in FIG. 6C) carries a microprocessor 132 (for example, a type 8032BH) for implemented tasks under the control of the host CPU 24. The second circuit board 124 includes the serial interface 188 (for example, a type MAX232) through which the host CPU 32 and test station microprocessor 132 communicate.

The second circuit board 124 also includes a static RAM block 176 (for example, a type 6264) for use by the microprocessor 132. The board 124 also carries a battery backed RAM block 178 (for example, a type 2816) for retaining information pertaining to the use and maintenance of the test station 12, which will be described in greater detail later. The board 124 also includes a programmable ROM block 180 (for example, a type 27C64). The ROM block 180 contains imbedded software that the host software 160 programs to instruct the microprocessor 132 to carry out prescribed test and certification procedures.

The second circuit board 124 carries the low voltage DC power (5 V) supply PS2 for the components on the second circuit board 124. As will be described in greater detail later, optical-isolation elements 198 carried on the first board 122 electrically isolate the low voltage components on the second board 124 from the high voltage electrical components 68 on the first board 122 and the solenoids 50/52. The control signals from the test station microprocessor 132 are channeled through the optical-isolators and decoded by decoders 202 before being sent to the drivers 204 for the relays 68 on the first board 122.

Likewise, optical-isolation elements 198 on the second board 124 electrically isolate the serial port interface 188 from its power supply PS1 carried on the first board 122.

The static RAM block 176, battery backed RAM block 178, and the ROM block 180 communicate with the microprocessor 132 via an address bus 182 and a data bus 184. Implementing the program in imbedded software, the test station microprocessor 132 transmits control signals through an I/O buss 186 (for example, a type 82C55) to activate the first and second solenoids 54/56 and the electrical components 68 on the first circuit board 122, as well as receive data signals from the electrical components 68, the pressure transducer 70, and the load cell 44. The second circuit board 124 carries an analog-to-digital (A-to-D) converter 190 (for example, a type ICL7135) that converts the analog signals of the pressure transducer 70, the lord cell 44, and the electrical components 68 on the first board 122 to digital signals for processing by the host CPU 24. The analog signals are conditioned and amplified by conventional front end conditioning circuits 192 on the second board 124. The conditioned analog signals are also preferably channeled through an analog multiplexer 194 (for example, a type 4051), which selects the analog signal to be converted by the converter 190. The digital output of the A-to-D converter 190 passes through a decoder 196, if necessary to assure compatibility with the microprocessor bus 186. The digital output is transmitted by the microprocessor 132 to the host CPU 32 for processing.

The second circuit board 124 also includes a watchdog 200 that alerts the operator should the microprocessor 132 fail during use. The details of the watchdog 200 will be described later.

The third circuit board 126 drives LED's exposed on the front panel 66 of the test station housing 36. The number and function of the LED's can vary. The illustrated and preferred embodiment provides five LED's (see FIG. 3 as well).

A status LED 134 identifies the test station 14 by a number 1 to 4 (when multiple test stations are being used), and blinks when tests are underway.

The moisture detection LED 110 (already described) illuminates when the spill detection element 100 in the wet chamber 40 senses liquid leakage.

A communication fault LED 136 illuminates when the communication link between the host processing station 12 and the test station 14 breaks down.

A device fault LED 138 illuminates when general electrical or logic failures in the test station circuitry are sensed.

A test power LED 140 illuminates when the outlet plug 144 of the test station 14 receives power.

Cables 142 lead around the dividing panel 38 between the dry and wet chambers 40 and 42 to electrically connect the first and second solenoids 54/56, the pressure transducer 70, the load cell 44, the spill detection element 100, and the proximity sensor 120 to the circuit boards 122, 124, and 126. Additional cables 142 also electrically connect a test station power plug 144 (mounted to the front panel 66 of the test station housing 36) and a ground probe 146 to the circuit boards 122, 124, and 126. In routing the electrical cables 142, high voltage lines are kept separate from low voltage lines.

Two resistance studs (designated S1 and S2) mounted on the dividing panel 38 extend into the wet chamber 40 (see FIGS. 4 and 6). The studs S1 and S2 are electrically connected to the boards 122, 124, and 126 in the dry chamber 42 to present different, known resistance values for conducting periodic ground resistance calibration at the prompting of the host CPU 24. The particularities of these calibration tests will be described later.

C. Start Up and Safety Checks

Preferably, the operator allows the test station 14 to warm up for a predetermined time (e.g. 5 minutes) before use. This warm up period allows the load cell 44 and other electrical components to stabilize before use.

The status LED 134 preferably displays a "–" indication or the like during the warm up period. After the warm up period, the status LED 134 displays the test station number. The displayed test station number is constant when the test station is on line but not being used to conduct a test. The displayed test station number blinks when the test station is on line and conducting a test, as previously described.

During power up, the test station microprocessor 132 runs a prescribed series of self tests during warm up to assure that communications with the host processing station 12 exists and that no general electrical or logic failures are present in the test station circuitry, including using checksum for battery backed RAM data. The test station microprocessor 132 illuminates the device fault LED 138 when general electrical or logic failures in the test station circuitry are sensed.

The test station microprocessor 132 also preferably includes a watchdog 200, as previously discussed. The watchdog 200 automatically interrupts operation of the test station 12 and initiates a power up routine after a given time-out period (for example 1.5 seconds), unless the watchdog receives a specified flag signal from the imbedded software on the second board 124, which resets the time-out period. When the microprocessor 132 is functioning properly, the watchdog 200 periodically receives the flag signal (for example, once every 0.5 second) to prevent its timing out. When the microprocessor 132 fails, the absence of the flag signal allows the watchdog 200 to time-out, initiating a power up routine to initiate the series of self-tests to identify the electrical or logic failure.

The test station microprocessor 132 also illuminates the communication fault LED 136 should communication with the host station 12 fail to be detected. The LED 136 goes off whenever communication occurs between the test station microprocessor 132 and the host CPU 24. Likewise, if communication is garbled, causing frequent transmissions and retransmissions, the LED 135 will flicker.

In addition, the host CPU 24 sends a periodic "heartbeat" signal to the test station microprocessor 132. The "heartbeat" signal causes the test station microprocessor 132 to transmit an elapsed test time signal. If the microprocessor 132 does not respond to the "heartbeat" signal, the host CPU 24 alerts the operator that communication with the test station 12 has broken down.

II. THE HOST PROCESSING STATION

A. The Host CPU

The host CPU 24 acts as the master of the system 10, initiating all of the control functions. The test station microprocessor 132 is slaved to the host CPU 24, as is the data reporting station 16, which respond to the control functions that the CPU 24 initiates. The host CPU 24 communicates with the test station microprocessor 132 and the data reporting station 16, as previously described. In this way, the host CPU 24 coordinates overall control functions for the system 10.

As FIG. 10 schematically shows, the host CPU 24 communicates with a mass storage device 148 (e.g., a hard drive) and an extended static RAM 150. Preferable, the RAM 150 includes a battery backup 152. The user interactive interface 154 (already described) also communicates with the host CPU 24.

The mass storage device 148 retains in non-volatile memory the databases and data processing intelligence to perform and process the intended test and certification procedures. In the illustrated and preferred embodiment (as FIG. 10 shows), the host CPU 24 retains in hard drive memory:

(1) a specification database 156 (see also FIG. 12), which contains the current physical, functional, and performance specifications of all makes and models of IV pumps that the system 10 is intended to test and certify, which are provided by or derived from the manufacturer's product specifications.

(2) a master test list database 158 (see also FIG. 13), which contains all visual, flow rate, occlusion, and electrical safety tests that the system 10 is capable of performing.

(3) the executable host program 160, which generates and implements the test matrix 162 (see FIGS. 14A and B) based upon the unique specifications for the make and model of the IV pump identified for testing by the system 10.

(4) a log file database 164 documenting by make, model, and unique identification designation, each pump tested by the system 10 and the results of each test and certification procedures conducted by the system 10 for each IV pump.

(5) a usage database 166 documenting usage of the host processing station and each test station it controls. Usage information can include, for example, the total number of automated test sequences completed by the host station 12; and the total number of test and certification procedures performed by each test station 14, classified according to test type.

The test station microprocessor 132 also retains usage information specifically relating to the test station in battery-backed RAM in the imbedded software of the test station microprocessor 132. This information can be retrieved by the operator upon demand through the host CPU 32. Representative examples of test station-specific usage information include the total times the test station 12 has been powered up; recent (e.g., the last twenty) test station error alarms; and recent (e.g., the last twenty) test station recalibrations performed by the operator (as will be described later).

In the illustrated and preferred embodiment, the host CPU 24 comprises a conventional 486-series microprocessor (33 Mhz or more), with a hard drive 148 having a mass storage capacity of at least 200 mB and RAM 150 of at least 4 mB.

B. Host Station Start Up

In readying the system 10 for use (as FIG. 1 shows), the operator supplies power to the host processing station 12, test station 14, and data reporting station 16.

Figure 11A:
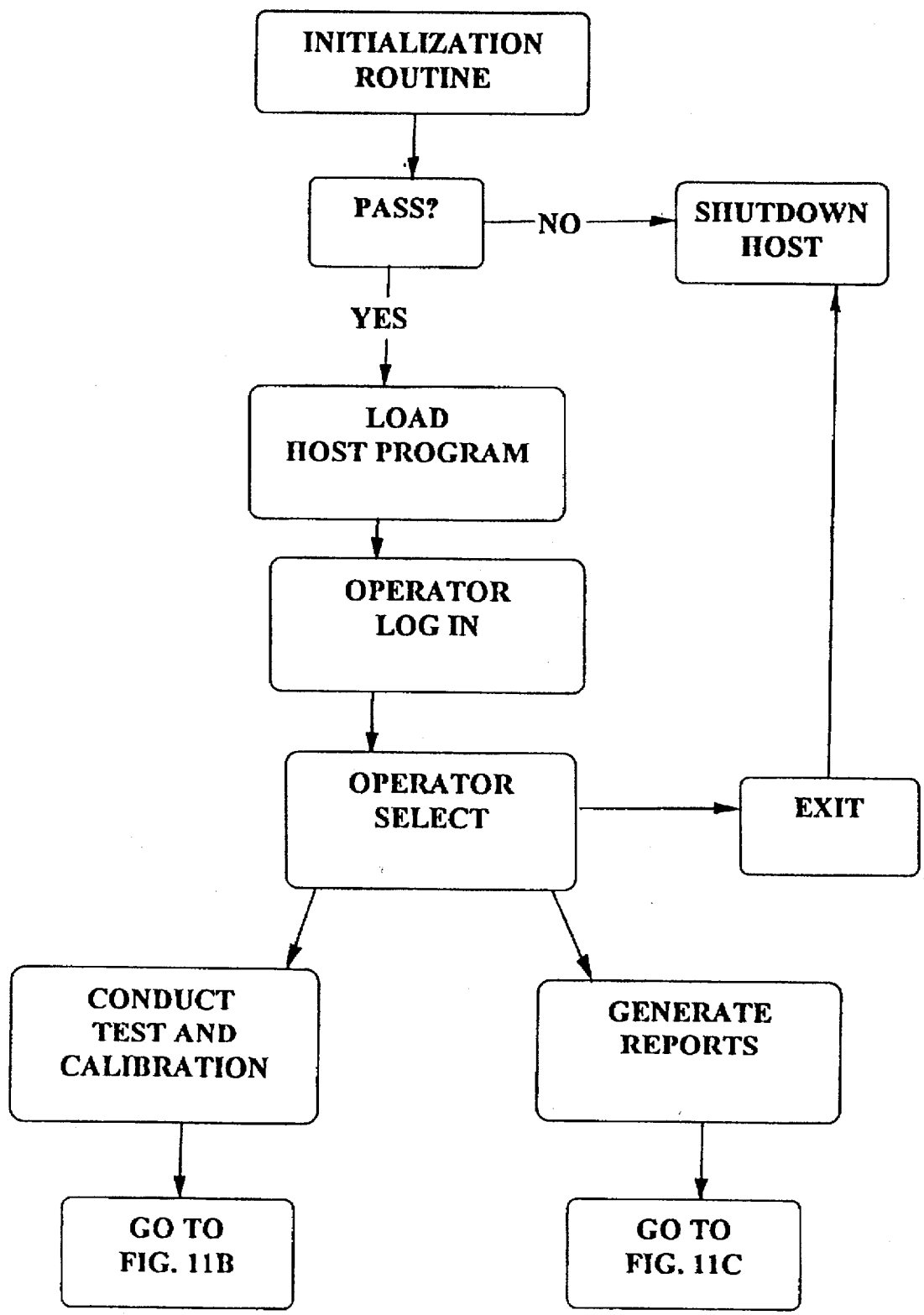
FIG. 11A is a schematic flow chart showing the operation of the host station CPU after start up and during the loading of the host program.

As FIG. 11A shows, like the test station microprocessor 132, the host CPU 24 conducts, upon start up, conventional initialization and critical data integrity checks (designated in FIG. 11A as the initialization routine) to verify that its processor and associated electrical components are working, including a checksum for battery backed RAM data.

If these power-up tests fail, the host CPU 24 enters a shutdown mode. Otherwise, the CPU 24 loads the host program 160.

Upon execution, the host program 160 prompts the operator to log on by verifying the correct date and time and identifying him or him or herself. Password protection could be implemented at this initial stage of the host program 160 to prevent unauthorized persons from using the system 10.

As FIG. 11A further shows, after log on, the host program prompts the operator to select among (a) Conducting a Test and Calibration Procedure; (b) Generating a Report; or (3) Exiting the Host Program.

C. Conducting a Test and Certification Procedure (1) Pump Identification

Figure 11B:
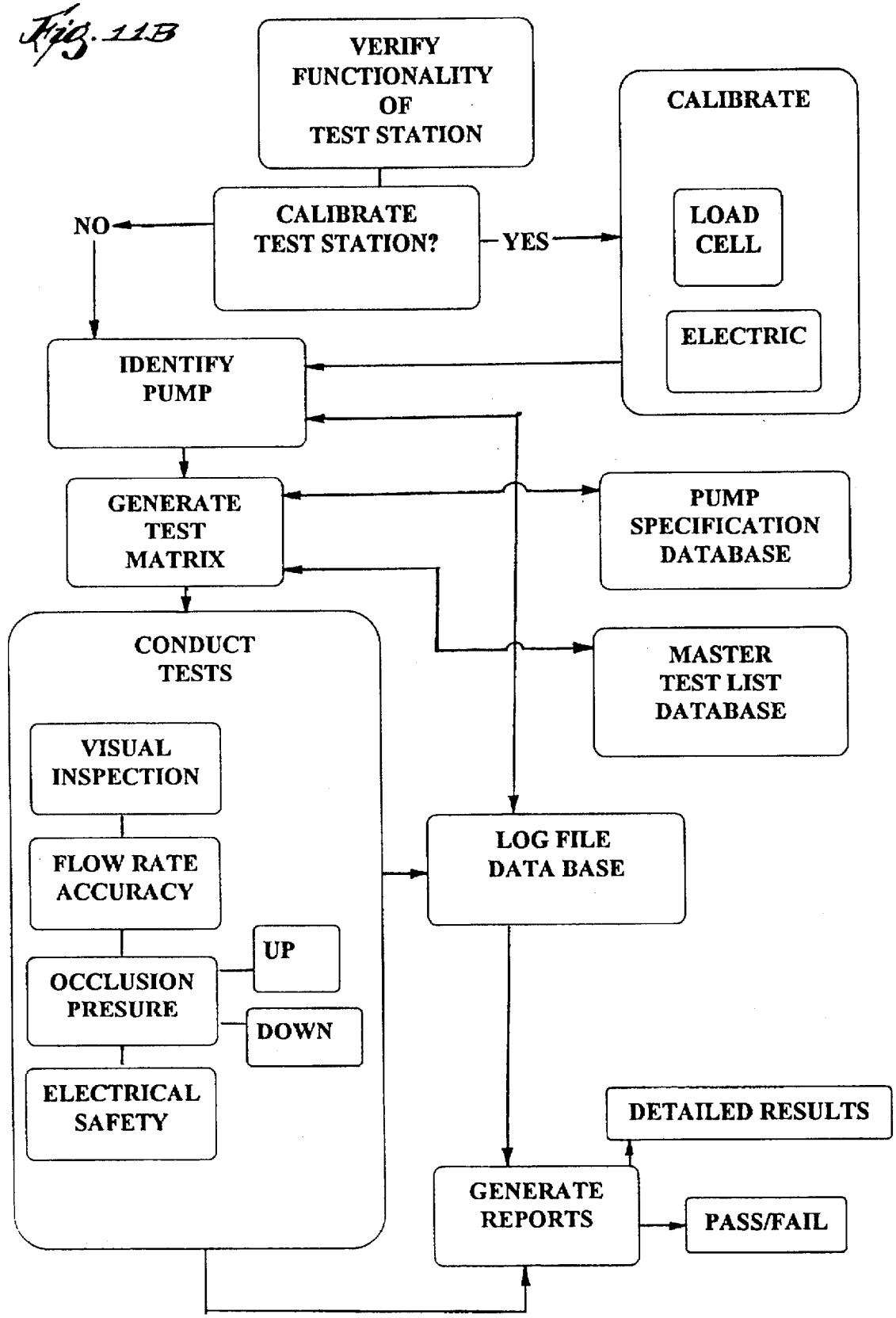
FIG. 11B is a schematic flow chart showing the operation of the host program in implementing a test and certification procedure.

As FIG. 11B shows, at the outset of each test and certification procedure, the host program 160 requires the operator to identify by make, model, and unique identification number the IV pump 20 to be tested. The operator responds by supplying an alpha-numeric designation unique to each IV pump tested by the system 10.

The designation can comprise the serial number assigned by the manufacturer of the IV pump. Alternatively, the designation can comprise an alpha-numeric sequence assigned by the user or distributor of the IV, or by the operator of the system 10.

The alpha-numeric designation is initially entered by the operator, upon prompting by the host program, by the keyboard 28. Alternatively, the designation can be entered by scanning the designation affixed in bar code form on a label attached to the pump. Once entered, the host CPU 24 retains the alpha-numeric designation in a file in the log file database 164. Thereafter, the operator can use the mouse 30 or keyboard 28 to open and scroll through pump identification windows displayed by the host program, which present those pumps recorded in the log file database 164. The operator can select one of the pumps using the mouse 30 or the keyboard 28.

The log file database 164 automatically generated by the host program 160 creates a historical record of all test and certification procedures conducted on the IV pump by the system 10, together with the detailed results of each procedure. The log file database 164 holds the log files for each IV pump, uniquely identified by its assigned alpha-numeric designation, thereby documenting the performance records and Pass/Fail diagnoses for all IV pumps tested by the system 10. It is from the log file database 164 that the host program compiles the performance and tests reports.

The automatic maintenance by the host program of the log file database 164 during each test and calibration procedure, coupled with the associated ability to generate reports both at the end of each test and certification procedure and on demand, constitutes an invaluable resource and management tool for the operator. Further details concerning these reports and the execution of host program in creating them will be described later.

(2) Generating the Test Matrix

As FIG. 11B shows, upon identifying the make, model, and alpha-numeric designation of the pump 20, the host program 160 creates and executes the test and certification procedure for the identified IV pump. The procedure first draws upon and consolidates information within the pump specification database 156 and the master test listing database 158 to create a test matrix 162 for the pump to be tested.

(A) Pump Specification Database

FIG. 12 is a representative excerpt from the specification database 156, listing the specifications for certain makes and models of commercially used IV pumps. As FIG. 12 shows, the specification database includes not only the functional and performance specifications for the pumps, but also the manufacturers' specifications regarding flow rate accuracy and occlusion pressure.

FIG. 12 shows that the specifications can differ significantly among different makes and models of pumps.

The specification database 156 can be periodically updated to remain current.

(B) Master Test Listing Database

FIG. 13 shows a listing of a representative master consolidated test database 158 retained by the host CPU 24. The host program 160 is capable of prompting the operator and directing the test station microprocessor 132 to implement all the tests in the master test database 158 according to prescribed criteria, as will be described later.

(C) The Test Matrix

Still, not all tests contained in the master consolidated test database 158 are applicable to all IV pumps. For example, as FIG. 12 shows, many IV pumps conduct liquid using only one pump channel, while other pumps have two pump channels. Therefore, the testing of a second pump channel found in the master database 158 (see Tests 27, 28, and 29) is simply not applicable to these pumps. As another example, pumps that are not AC powered do not require the electrical safety tests listed in the master database 158.

Therefore, before proceeding with testing a given IV pump identified by the operator, the host program 160 correlates the information contained in the master consolidated test database 158 based upon the information contained in the specification database 156 for the pump identified for testing. This correlation generates the test matrix 162 (see FIGS. 14A and B) for the identified IV pump.

FIGS. 14A and B show representative text matrixes 162 for the IV pumps contained in the specification database 156 shown in FIG. 12, based upon the master test database 158 shown in FIG. 13.

The pump-specific test matrix 162 takes into account the particular functional and performance characteristics of the identified IV pump set forth in the specification database 156. The matrix 162 selects from the master consolidated test database 158 only those tests that can or should be performed on the identified pump during the test and calibration procedure (see FIG. 14A). The test matrix 162 also takes into account the accuracy flow rate and occlusion flow rate and pressure data set forth in the specification database 156 for identified pump (see FIG. 14B).

Guided by the test matrix 162 for the particular IV pump identified for testing, the host program 160 proceeds with the test and calibration procedure. As FIG. 11B shows, the procedure advances through visual inspection tests, flow rate accuracy tests, occlusion pressure tests, and electrical safety tests set forth in the pump-specific test matrix 162. The host program 160 also uses the flow rate accuracy and occlusion flow rate and pressure information specified for that IV pump in the test matrix 162 in setting up and evaluating the flow rate accuracy tests and occlusion pressure tests. The host program 160 also draws upon information in the test matrix 162 to recommend the flow rate for conducting the accuracy tests, as well as the number of flow rate samples that should be taken during the test period.

A given IV pump receives an overall PASS result for the test and calibration procedure only if it receives a PASS result for every visual inspection test, every flow rate accuracy test, every occlusion pressure test, and every electrical safety test contained in its test matrix 162. Otherwise, the IV pump receives an overall FAIL result for the test and calibration procedure.

The overall nature of the individual tests on the master list database 158 that are implemented by the host program 160 in the illustrated and preferred embodiment will now be discussed in greater detail.

(3) Conducting Visual Inspection Tests

The host program 160 carries out visual inspection tests by prompting the operator to operate and/or visually inspect certain physical or functional aspects of the IV pump that are accessible or visible to the operator.

The particular aspects of the IV pump identified for operation or inspection in the test matrix 162 during the visual inspection tests can vary according to the particular specifications of the pump. The following is a representative listing of typical visual inspection tests and the associated representative prompts that the host program can use:

Unit Clean
Host Program Prompt:
Ensure the pump is clean of all spilled fluids and other dirt or grime. Check for solution stains in corners and connections between case halves and/or other assemblies.

Loose Component (Vibration) Check
Host Program Prompt:
Listen for loose components moving around the inside of the pump while turning the pump upside down and sideways. During Flow Rate Accuracy testing, check for excessive vibration or other noises emanating from the pump.

Keypad & Display Window (Visual Check)
Host Program Prompt:
Check for cuts, cracks, or holes in the keypad or display window. Check for fluid on the inside of the display window. Ensure that any scuffs or other marks on the display window do not interfere with the correct reading of the display.

Case Assembly
Host Program Prompt:
Visually inspect the pump case for missing or damaged parts including any cosmetic defects.

Battery Door Inspection
Host Program Prompt:
The battery door should slide upward to reveal the battery compartment. Verify some resistance at the start of opening and smooth operation once started. Ensure that the battery diagram symbol with the + and − symbols is firmly in place. Ensure that the battery contact pads are firmly in place.

Latch Assembly Inspections
Host Program Prompt:
Verify smooth operation for the Channel A latch and the Channel B latch. In opening a latch, it should move in an "L" shape by sliding down and then back. To close the latch, slide down, forward and then up. The small tab on the latch assembly should overlap the small tab on the administration set cartage and hold the cartridge in place.

Power Up On Battery
Host Program Prompt:
Install both batteries. Tone alarm will beep and the LCD will display:
UNIT SELF TEST IN PROGRESS
At the completion of the self-test, the display will then show the results of the last program entered and "STOP."

Ensure all LCD segments are visible.
Press the [DISPLAY] key. Verify that backlight is illuminated.
Verify that the pump powers on with one battery in either battery position. Shake pump to verify continued battery operation. Try each battery position one at a time.

Keypad Functionality
Host Program Prompt:
Activate each key to ensure it correctly responds and operates. Ensure correct information is displayed with each key activation. Inspect for excessive wear of keys.

Prime Buttons Functionality
Host Program Prompt:
Place pump in priming mode. Depress [PRIME] button followed by pressing and holding the A channel button.. Ensure the Channel A motor turns and set priming function is initiated and properly completed. Depress [PRIME] button followed by pressing and holding the B channel button.. Ensure the Channel B motor turns and set priming function is initiated and properly completed.

Bolus Button Functionality
Host Program Prompt:
Place pump in bolus delivery mode. Depress bolus button. Ensure bolus delivery is initiated and properly completed.

Remote Bolus Cord Functionality
Host Program Prompt:
Attach Remote Bolus Cord to pump. Verify that display does not change while plug is being inserted. Place pump in bolus delivery mode. Depress remote bolus button. Ensure bolus delivery is initiated and properly completed.

Air In Line Detectors
Host Program Prompt:
Visually inspect for excessive wear or damaged parts on the air detector transmitter and receiver for both Channel A and Channel B.
Verify that the air alarm is not defeated. To verify, ensure that each channel is programmed. Press the [DISPLAY] key and note that:
"AIR IN LINE *A"
"ALARM ON" and
"AIR IN LINE *B"
"ALARM ON"
is displayed on the screen.
Enter air bubble into administration set above the pump mechanism for Channel A. Air bubble size must be greater than 50 to 100 microliters. Ensure air bubble is detected and that the air alarm is properly indicated by "AIR" in the display and is accompanied by a beeping tone alarm.
Clear the alarm. Enter air bubble into administration set above the pump mechanism for Channel B. Air bubble size must be greater than 50 to 100 microliters. Ensure air bubble is detected and that the air alarm is properly indicated by "AIR" in the display and is accompanied by a beeping tone alarm.

Memory Check
Host Program Prompt:
Remove batteries from pump for 15 seconds.
Display should go blank.
Reinstall batteries.
Following completion of the pump self-test, press the [DISPLAY] key and verify that the previous program is displayed.

Proper Labels
   Host Program Prompt:
      Visually inspect to ensure no labels are damaged beyond use or exhibit excessive wear.
      Visually inspect to ensure the pump has attached to it all appropriate product labels in the correct locations. At minimum, this is to include:
         Name Plate Label
         Side Logo Label
         Operating Instructions Label
         Warranty Void Label
         Bolus Label
Final Visual Inspection
   Host Program Prompt:
      Visually inspect the pump to ensure no scratches, blemishes or other physical damage has occurred during the course of testing or was otherwise not noted during previous inspections.
      Ensure all required labels are present with technician initials and dates where appropriate.
      If appropriate, attach recertification label.
Documentation Complete
   Host Program Prompt:
      Ensure all required recertification documents are present.
      Ensure all required recertification documents are correctly and completely filled in.
      Ensure signatures are in appropriate areas.
Power Up on AC Power
   Host Program Prompt:
      Plug the pump power plug into the power receptacle on the Test Station. Connect the ground probe to a chassis grounded conductive part. Turn the pump power switch on.

In addition to a visual prompt, the host program 160 may also include a graphic display of information to instruct the operator in performing the visual test.

The operator responds to the host program's prompts individually for each visual test item by indicating compliance (PASS) or lack of compliance (FAIL), using either the keyboard 28 or clicking the mouse 30 to enter information. Preferably, the host program 160 does not proceed with other tests categories on the test matrix 162 until the operator has appropriately responded to all the visual inspection prompts.

A preferred implementation of the host program 160 (see FIG. 24A) includes a VISUAL TEST MENU which displays the visual tests and provides Fail and Pass Buttons. The operator makes the selections, as appropriate, by clicking the mouse.

This preferred implementation also provides a Detail Button (as FIG. 24A shows), which the operator can click to open a help window (see FIG. 24A). The help window (which FIG. 24B shows for the Pole Clamp Test) explains to the operator the how the visual and functional inspection should be carried out for the particular test. The Host Program Prompts, listed above, are found in the help windows for their respective test items.

Only if all selected visual inspection test items receive a PASS response does the host program 160 register a PASS result for the overall visual inspection test. Otherwise, the host program registers a FAIL result.

In a preferred implementation, the VISUAL TEST MENU lists only those tests that can be accomplished before the pump 20 is either electrically coupled to or placed in liquid flow communication with the test station 14. Tests that are not dependent upon connection to the test station 12 include, for example, Test Numbers 1 to 8 and 11 to 21 in the master test listing database shown in FIG. 13. These tests are preferably performed at the outset of the test and calibration procedure, with prompting by the host program 160, while the pump 20 is free of attachment to the test station 14. Because of this, after completing all required tests, the operator can exit the VISUAL TEST MENU without completing any of the remaining tests in the test matrix 162. The host program 160 nevertheless establishes and retains in the log file database 164 for that pump the results of the completed visual tests. At a later time, the operator can enter the host program 162 and resume the test and certification procedure for that pump, skipping the visual tests already performed. In this way, an operator having a limited number of available test stations can conduct simultaneously the functional/visual tests on one pump (without attachment to a test station) while another pump (attached to a test station) undergoes testing.

(4) Conducting Liquid Conveyance Tests

To conduct flow rate accuracy tests and occlusion pressure tests, the pump 20 must be coupled in liquid flow communication with the test station 14, as well as must be electrically coupled to the test station 14.

The host program 160 prompts the operator to install a primed disposable administration set 168 intended for the IV pump 20. In carrying out this instruction (see FIG. 1), the operator connects the proximal end of the set 168 to a full solution bag 170 suspended above the pump 20 for gravity flow. The operator connects the male luer at the distal end of the set 168 to the female luer 64 on the front panel 66 of the test station housing 36. The operator also readies the drain tube 82 by routing it from the test station 14 to a suitable drain receptacle 172. Preferable, the operator is prompted to prime the set using about 2 mL of liquid.

If the pump 20 is AC powered, the operator will also be prompted to connect the AC power cord 174 of the IV pump 20 to the power outlet 144 on the front panel 66 of the test station housing 36 (see the Power Up on AC Power Test, described above). At the same time, the operator will further be prompted to connect the ground continuity probe 146 of the test station 14 to a suitable connection site on the IV pump 20, such as a ground lug or to the handle or the IV pole on the stand 22 carrying the IV pump 20.

(a) Test Station Verification

As FIG. 11B shows, at some point before beginning a prescribed liquid conveyance test, the host program 160 preferably verifies that the first and second solenoids 54 and 56 in the wet chamber 40 of the test station 14 are functional, not leaking, and ready for operation.

With the first solenoid 54 and second solenoids 56 in their unactivated position (as FIG. 15 generally shows), the host program 160 prompts the operator to turn on the pump 20 to convey fluid into the wet chamber 40. If the load cell 44 does not sense the expected increase in weight of the bottle 48, either the first or second solenoids 54/56, or both, are presumed to have failed in their activated positions.

The host program 160 can direct the test station microprocessor 132 to supply trouble shooting information to identify the failure mode and prompt the operator accordingly. For example, with minimal pressure sensed by the pressure transducer 70, the host program 160 deduces the second solenoid 56 as the source of failure. With high pressure sensed by the pressure transducer 70, the host program 160 deduces the first solenoid 54 as the source of failure.

With the first solenoid 54 in its activated position (as FIG. 16B generally shows), the pressure transducer 70 should sense an increase in pressure. If the pressure transducer 70 does not sense this expected pressure increase, the host program 160 deduces that the first solenoid 54 has failed in its unactivated position and prompts the operator accordingly.

When the second solenoid 56 is in its activated position (as FIG. 17 generally shows), liquid should drain from the collection bottle 48, and the load cell 44 should sense a decrease in weight. If the load cell 44 does not sense this expected decrease, the host program 160 deduces that the second solenoid 56 has failed in its unactivated position and prompts the operator accordingly.

If either solenoid 54 or 56 has failed in a leaky condition, the spill detector element 100 will sense the presence of liquid. The test station microprocessor 132 senses this condition and relays a "liquid leakage" signal to the host program 160, which alerts the operator.

When these threshold functionality tests indicate the readiness of the test station 14, the host program 160 proceeds stepwise through the applicable flow rate accuracy tests and occlusion pressure tests.

(b) Flow Rate Accuracy Tests

The host program 160 carries out the flow rate accuracy tests by operating the pump 20 to convey liquid of a known specific gravity to the collection bottle 48 in the wet chamber 40, while monitoring the change in weight sensed by the load cell 44 over time.

Figure 15:
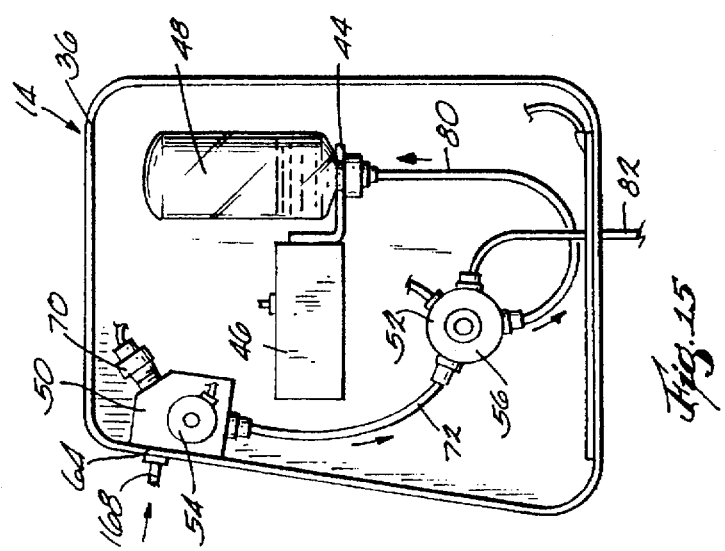
FIG. 15 is a side elevation view of the wet chamber of the test station, largely in schematic form, during the performance of a flow rate accuracy test.

More particularly, as FIG. 15 shows, with the IV pump 20 operating, the host program 160 directs the test station microprocessor 132 to retain the first and second solenoids 54/56 in their normal, unactivated conditions. Liquid conveyed by the IV pump 20 flows through the inlet and drain valve stations 50 and 52 into the collection bottle. The test station microprocessor 132 converts the analog weight signals received from the load cell 44 during successive prescribed sample periods to digital weight signals. The digital weight signal from one sample period are compared to the weight signal for a preceding sample period. By assessing the change in weight between the sample periods, and knowing the specific gravity of the liquid being conveyed, the host CPU 24 gravimetrically calculates a flow rate at the end of successive sample periods during the test period.

The host program 160 defaults to a recommended flow rate, an overall test period for the accuracy test, and a recommended weight sample period within the test period. The host program 160 selects these based upon the particular specifications for accuracy of the IV pump 20 undergoing testing, as set forth in the test matrix 162 generated for the pump 20. The selected test and sample periods take into account the flow conditions encountered during normal use of the particular pump.

For example, one pump (like a Pharmacia Deltec™ Model CADD-5800) operates at relatively a low flow rate of 20 mL/hr in normal use. Another pump (like a Pharmacia Deltec™ Model CADD-5101HF) operates at a relatively high flow rate of 299 mL/hr in normal use. The host program 160 requires longer test and sampling periods for lower flow rates, to thereby preserve a high degree of accuracy (preferably less than 1%) during testing. Therefore, the preselected test and sample periods for the lower flow rate pump are longer than the selected test and sample periods for the higher flow rate pump. Likewise, the selected test and sample periods for the lower flow rate pump are longer than the selected test and sample periods for the higher flow rate pump.

Still, the host program 160 preferably allows, within a reasonably prudent range of acceptable test and sample periods, the operator to change the selected test and/or sample period in his/her discretion.

The host program 160 also defaults to the specific gravity of water as the liquid to be used for the flow rate tests. The host program 160 also allows the operator to select another liquid (for example, a TPN solution) and alter the specific gravity according.

Under the direction of the host program 160, the host CPU 24 processes the changes in the digital weight signals during successive sample periods to gravimetrically calculate the flow rates periodically throughout the test period.

Figure 18:
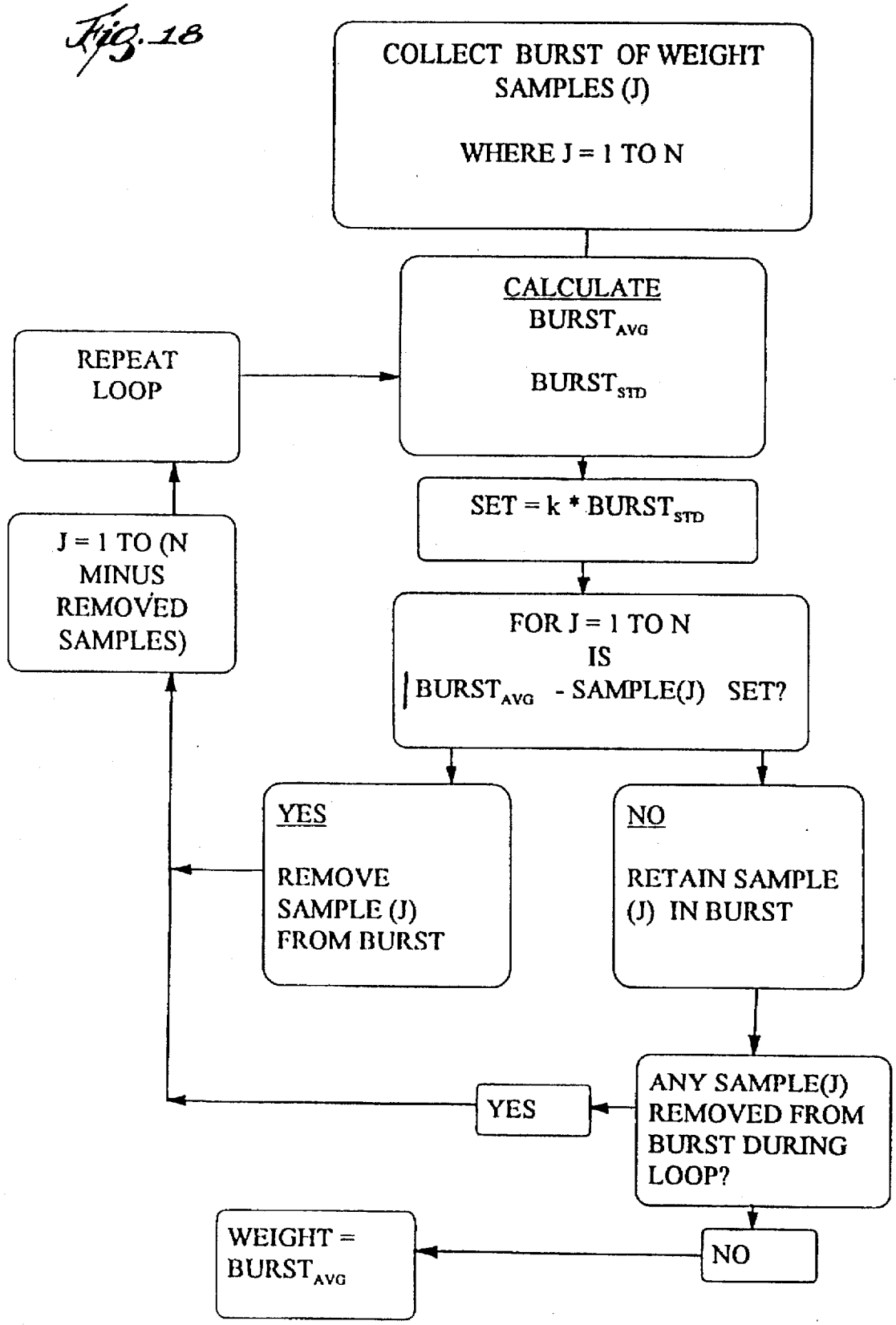
FIG. 18 is a schematic flow chart showing the operation of the host program in burst filtering load cell weight samples to derive an average weight measurement for use in determining flow rate accuracy.

In the illustrated and preferred embodiment (see FIG. 18), the host CPU 24 uses a "data burst" technique to filter multiple digital weight samples over each sample period. More particularly, the host CPU 24 takes a prescribed number (n) of digital weight samples (a "data burst" of n data samples, or SAMPLE(J), where J=1 to n) during each sample period. Preferably, the bursts are clustered at the end of the sample period. For example, given a sample period of about 1 minute, the data burst of five samples is begun at about the 58th second of the period. After the five data samples within the burst are taken (at about 0.5 seconds per data sample), a new sample period is initiated.

The host CPU 24 then calculates an average ($BURST_{AVE}$) and a standard deviation ($BURST_{STD}$) of the n samples in the burst. The CPU 24 then compares each of the n samples (SAMPLE (J), for J=1 to n) and rejects a SAMPLE(J) when the absolute value of $BURST_{AVE}$–SAMPLE(J)>SET, where SET=k*$BURST_{STD}$, k being a preselected value. In the preferred embodiment, k is 1.5.

Upon rejecting one or more SAMPLE(J) within the burst based upon this criteria, the CPU 24 again calculates $BURST_{AVE}$ and $BURST_{STD}$ for the remaining samples within the burst (J now equalling 1 to the value of n minus the number of samples rejected). The CPU 24 again reviews the remaining samples to determine whether each meet the selected standard deviation variance. The CPU 24 continues to reject samples that fall outside the standard deviation variance and recalculate a new $BURST_{AVE}$ and $BURST_{STD}$ for the remainder of the samples, until all samples remaining the burst meet the standard deviation variance criteria. $BURST_{AVE}$ after such processing is then used as the weight for calculating flow rate at the end of each sample periods.

The CPU 24 compares the actual flow rate data derived during the test period to prescribed flow rate criteria. The prescribed flow rate criteria are selected based upon the flow rate accuracy specified by the manufacturer for the particular pump undergoing testing, which is set forth in the test matrix 162 (see FIG. 14B). Based upon this comparison, the CPU 24 determines whether or not the processed actual flow rate data meets the criteria established by the manufacturer.

Figure 19:
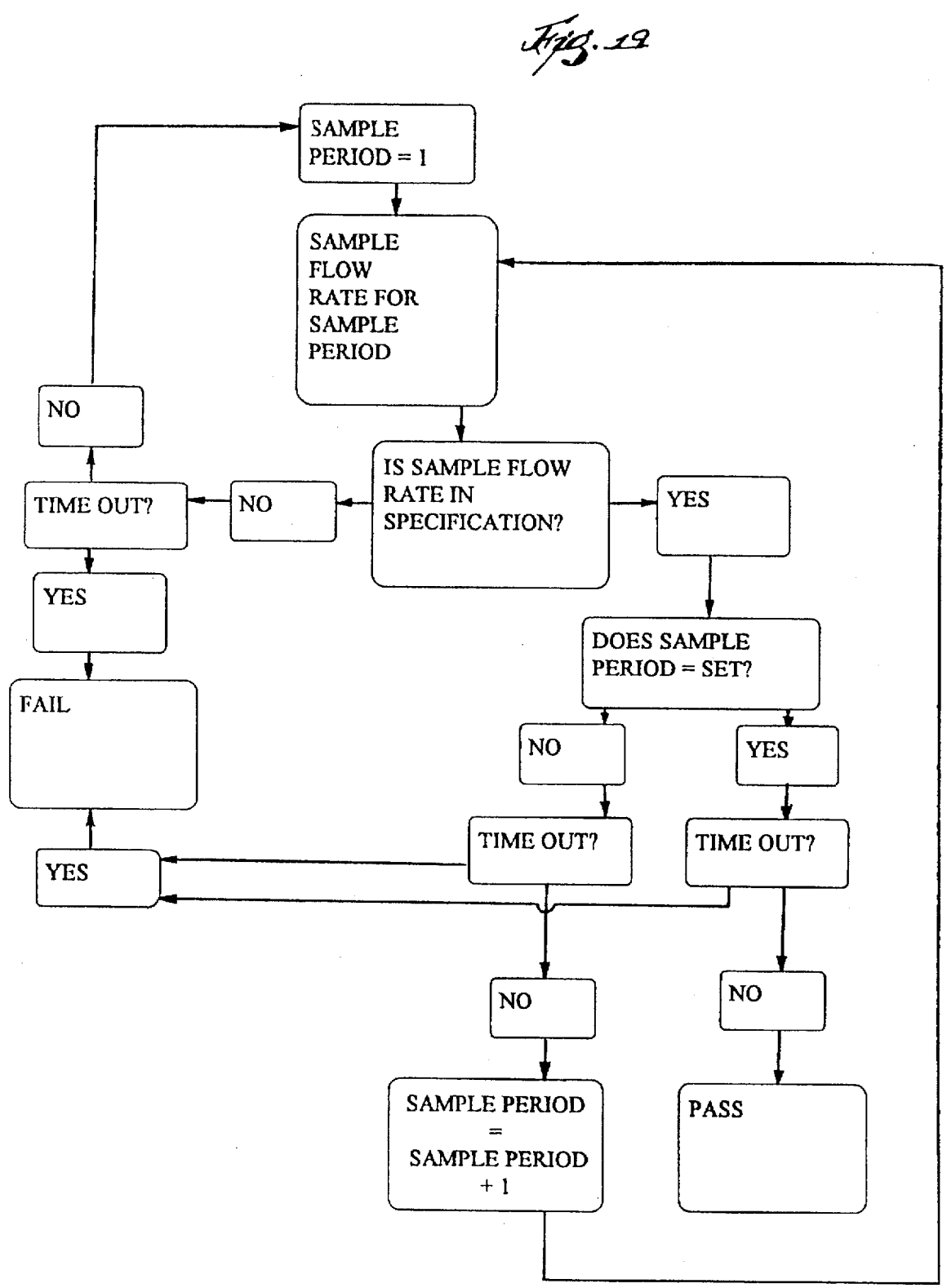
FIG. 19 is a schematic flow chart showing the operation of the host program in determining whether the pump undergoing testing meets the overall flow rate accuracy tests.

In the preferred embodiment (see FIG. 19), the CPU 24 makes this determination based upon the overall accuracy of the IV pump during the test period. More particularly, to meet the established criteria, the CPU 24 requires that a prescribed number of flow rates sampled at consecutive sample periods during the test period fall within the manufacture's specified range of accuracy during the test period. The host program selects the prescribed number of consecutive samples based upon the set flow rate during the test period.

Still, the host program 160 allows, within a window of acceptable values, the operator to change the number of flow rate samples required in his/her discretion.

If the specified number of consecutive flow rates sampled during the test period fall within the range of flow rates specified in the test matrix 162, the host program 160 registers a PASS result. Otherwise, the host program 160 registers a FAIL result.

Figure 25:
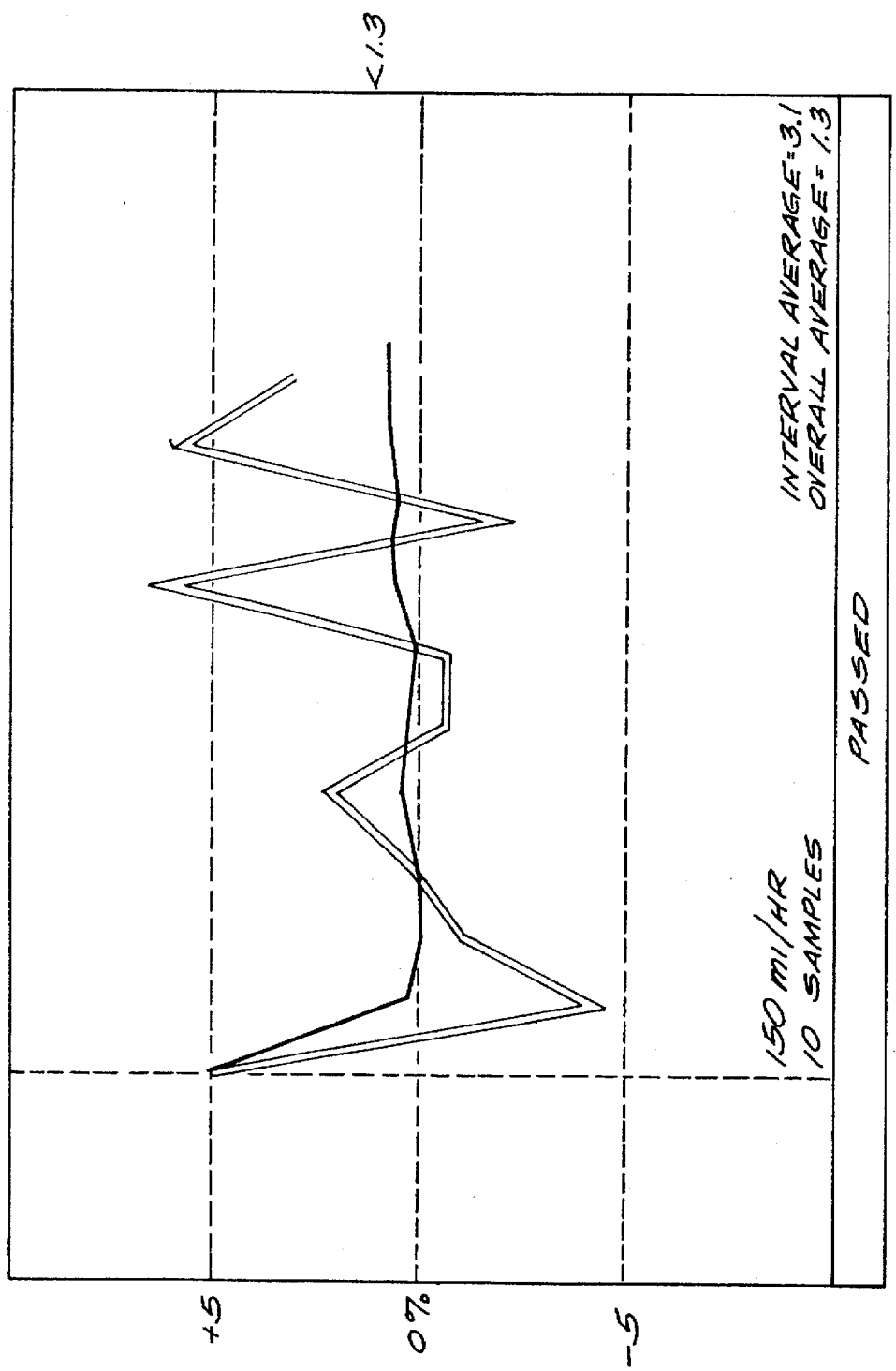
FIG. 25 is a visual real time display of the flow rate accuracy test used in a preferred implementation of the host program.

In a preferred implementation, the host program graphically displays the flow rate accuracy test in real time as the test proceeds. FIG. 25 shows a representative graphical display. The graphical display shows time on the horizontal axis and percent above and below the accuracy flow rate set by the test matrix on the vertical axis. The manufacturer's specified range of accuracy (in percentage), as also set by the test matrix, is bounded by horizontal lines extending above and below the zero percent axis. In FIG. 25, the specified range of accuracy is plus/minus 5%.

The graphical display in FIG. 25 plots the interval average as well as the overall average as a function of time. FIG. 25 shows an overall average of +1.3% for the test period. The overall average is also continuously graphically displayed as a floating icon on the right hand side of the display throughout the test period. In FIG. 25, the pump achieved a PASS result.

(c) Occlusion Pressure Tests

The host program 160 carries out the occlusion pressure tests by prompting the operator to simulate an upstream occlusion (between the solution bag 170 and the IV pump 20) and by operating the test station 12 to simulate a downstream occlusion (between the pump 20 and the patient). The IV pump 20 must pass both upstream and downstream occlusion tests to pass the overall occlusion pressure tests.

(i) Upstream Occlusion Test

Figure 16B:
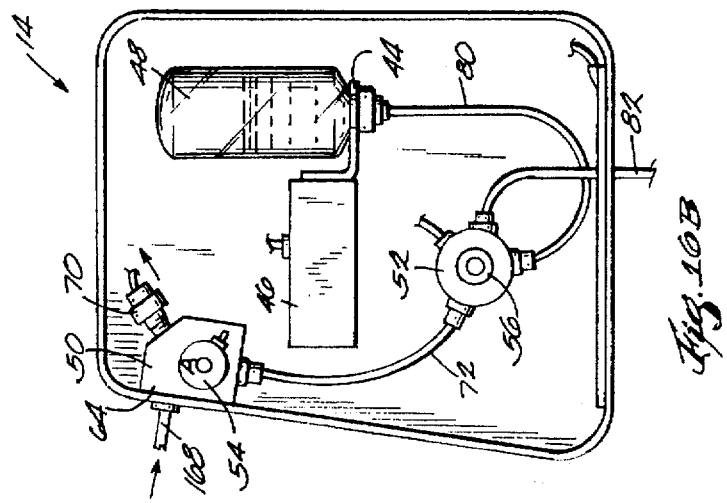
FIG. 16B is a side elevation view of the wet chamber of the test station, largely in schematic form, during the performance of a downstream occlusion pressure test.
Figure 16A:
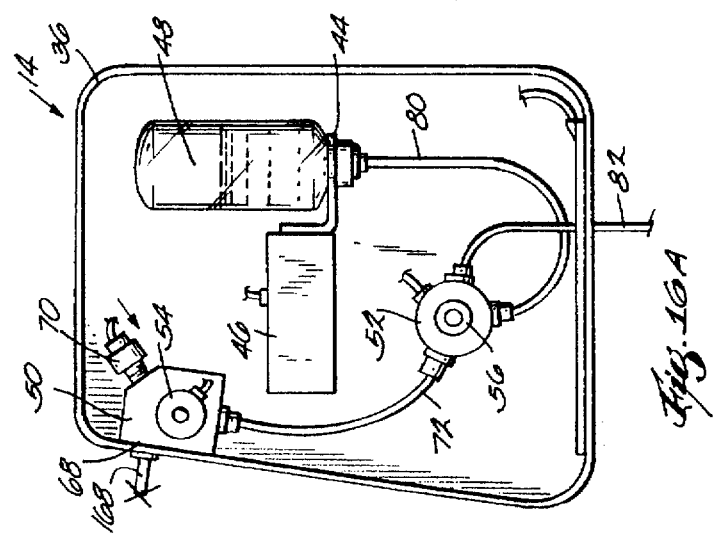
FIG. 16A is a side elevation view of the wet chamber of the test station, largely in schematic form, during the performance of an upstream occlusion pressure test.

In carrying out the upstream occlusion tests (see FIGS. 16A and 20A), the host program 160 prompts the operator to clamp the upstream tubing 168 close while the IV pump is operating, thereby simulating an upstream occlusion (see FIG. 16A). The operator is prompted to notify the host program 160, either by using the mouse 30 or the keyboard 28, when the occlusion alarm of the pump 20 sounds.

Figure 20A:
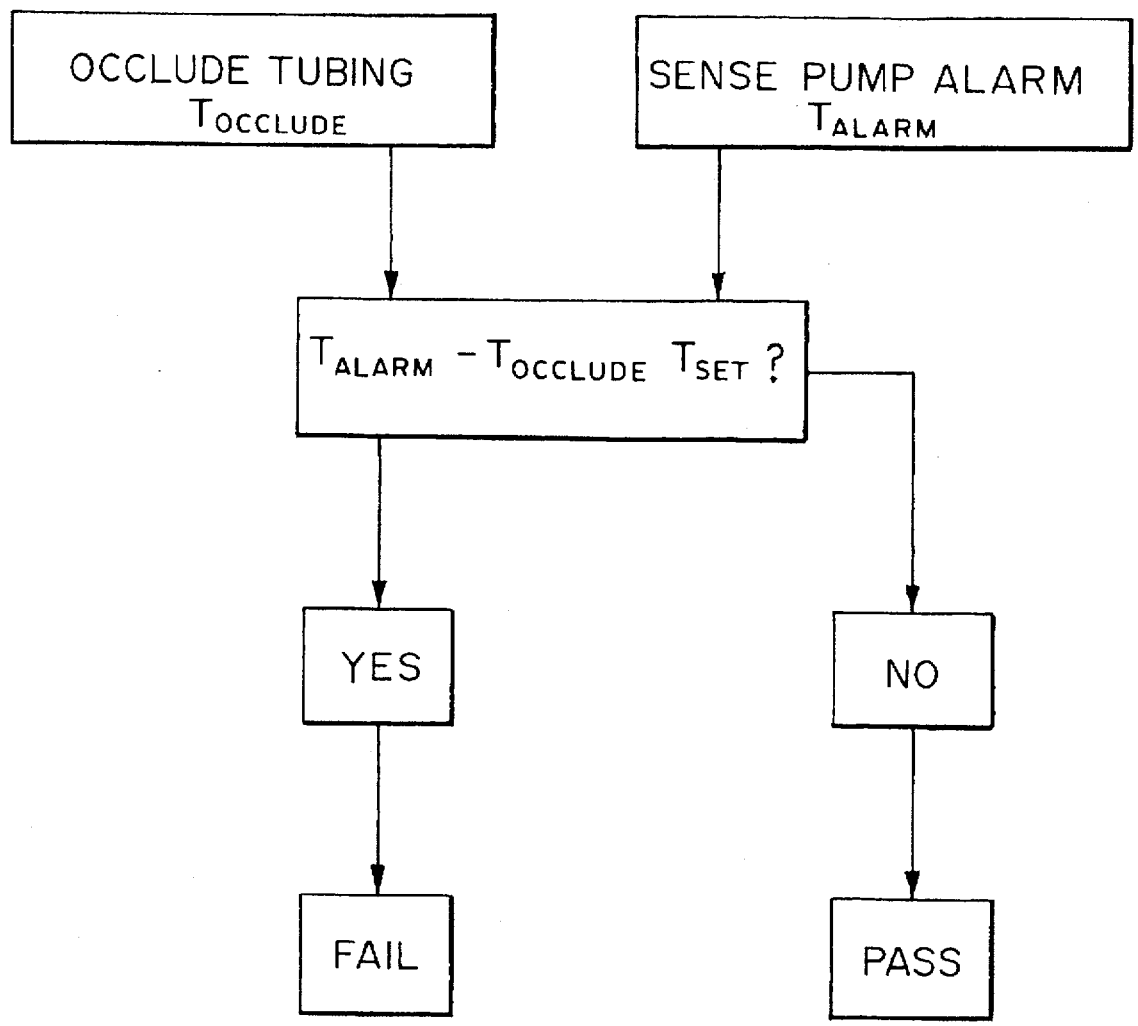
FIG. 20A is a schematic flow chart showing the operation of the host program in determining whether a pump undergoing testing passes the upstream occlusion tests.

The host program 160 measures the time interval between the simulated upstream occlusion $T_{OCCLUDE}$ and the time $T_{ALARM}$ at which the operator indicates the alarm has sounded (see FIG. 20A). The host program 160 compares the measured time interval $T_{ALARM} - T_{OCCLUDE}$ prescribed time period $T_{SET}$ that the host program 160 sets according to the manufacturer's specification for the IV pump. If the measured time period falls within the specified time period, the host program 160 registers a PASS result. Otherwise, the host program 160 registers a FAIL result.

(ii) Downstream Occlusion Test

Figure 20B:
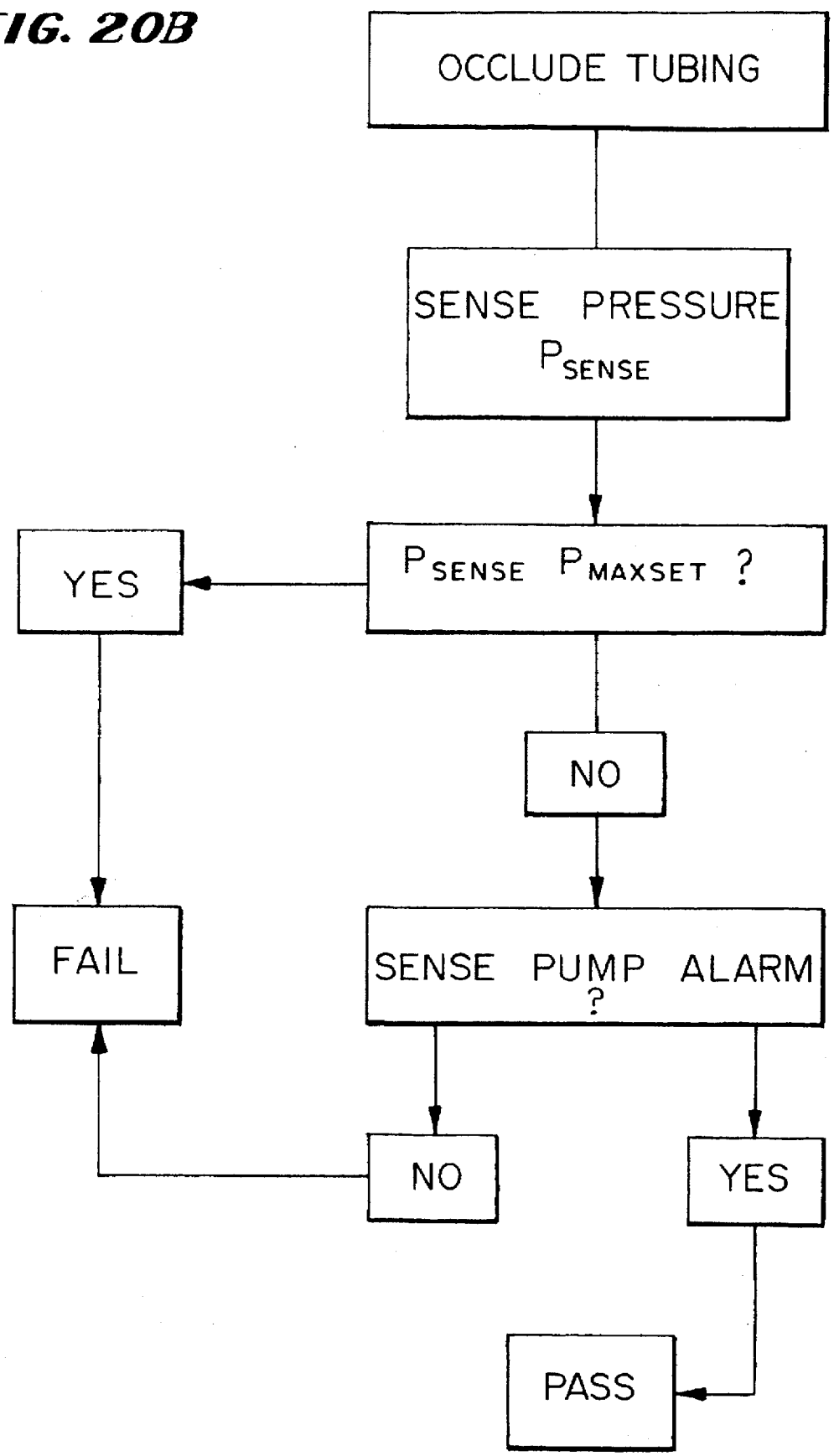
FIG. 20B is a schematic flow chart showing the operation of the host program in determining whether a pump undergoing testing passes the downstream occlusion tests.

In carrying out the downstream occlusion tests (see FIGS. 16B and 20B), the host program 160 prompts the user to operate the pump 20 at a specified flow rate to convey liquid to the collection bottle 48 in the wet chamber. The host program directs the test station microprocessor 132 to activate the first solenoid 54. In this condition (see FIG. 16B), liquid conveyed by the IV pump 20 cannot flow beyond the inlet valve station 50, thereby simulating a downstream occlusion. The operator is prompted to notify the host processing station, either by using the mouse 30 or the keyboard 28, when the occlusion alarm of the pump 20 sounds.

During the simulated downstream occlusion, liquid pressure builds in the second branch 60 of the inlet valve station 50, as FIG. 16B shows. The pressure transducer 70 senses the increasing pressure. The test station microprocessor 132 converts the analog pressure signals received from the pressure transducer 70 to digital signals, which are sent to the host CPU 24.

During the downstream occlusion, the host program 160 continuously monitors the pressure sensed by the pressure transducer 70 $P_{SENSE}$. The host program 160 continuously compares the measured pressure $P_{SENSE}$ to a prescribed maximum pressure $P_{MAXSET}$ that the host program 160 sets. $P_{MAXSET}$ can be set by the host program 160 according to the manufacturer's specification for the given IV pump, or it can be set by the host program 160 at a generic value (e.g. 36 PSIG) applicable to IV pumps in general. If any pressure reading $P_{SENSE}$ sensed during the test interval set by the host program 160 exceeds the maximum set for the pump $P_{MAXSET}$, the host program 160 immediately registers a FAIL result.

If the measured sensed pressure $P_{SENSE}$ does not exceed the specified minimum pressure $P_{MAXSET}$ during the test interval, the host program 160 prompts the operator to indicate whether the pump occlusion alarm sounded during the test interval. If the operator provides input that the occlusion pump alarm did sound during the test period, the host program 160 registers a PASS result. However, if the operator occlusion pump alarm does not go off during the test period, the host program 160 registeres a FAIL result, even when the measured sensed pressure $P_{SENSE}$ does not exceed the specified minimum pressure $P_{MAXSET}$ during the test interval.

In a preferred implementation, the host program 160 consolidates the time and pressure sensing aspects of the test in an intuitive graphical display, which is presented in real time as the tests proceed.

Figures 26A, 26B:
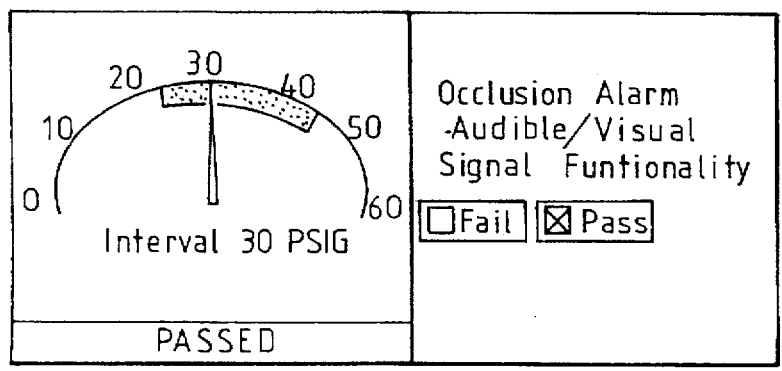
FIG. 26A is a visual real time display of the occlusion pressure test used in a preferred implementation of the host program.
FIG. 26B is a visual real time display of the occlusion alarm time test used in a preferred implementation of the host program.

FIG. 26A shows a representative graphical display during the upstream occlusion test. The display depicts a digital timer that begins at $T_{SET}$ and counts down to zero. The operator clicks the PASS button as soon as the occlusion alarm sounds. If the PASS button is clicked before the time runs out on the timer, the pump receives a PASS result for the downstream occlusion test. FIG. 26A shows a countdown timer originally set at 5:00 minutes. FIG. 26A shows that the occlusion alarm sounded within six seconds, the digital timer having counted down in real time from 5:00 minutes ($T_{SET}$) to 4:54 minutes.

FIG. 26B shows a companion display for the downstream occlusion test. The companion display depicts a pressure gauge showing the instantaneous, sensed pressure during the test interval. FIG. 26B shows this sensed pressure to be 30 PSIG, less than the $P_{SET}$ of 36 PSIG. The display also shows that the occlusion alarm sounded during the test interval, as the operator has checked the Pass button next to the gauge.

FIGS. 26A/B show the pump to have passed both the upstream and downstream segments of occlusion pressure test.

If the host program 160 registers a PASS result for both the upstream and the downstream occlusion tests, the host program 160 registers an overall PASS result for the occlusion pressure tests. If the host program registers a FAIL result for either the upstream occlusion test or the downstream occlusion test, the host program 160 registers an overall FAIL result for the occlusion pressure tests.

Upon completing the occlusion pressure tests, the host program 160 directs the test station microprocessor 132 to deactivate the first solenoid 54 to relieve the simulated downstream occlusion.

(d) Test Station Drain

At some point after completing all liquid conveyance tests using the test station 14, the host program 160 directs the operator to turn off and disconnect the IV pump 20 from the test station 14. The host program 160 directs the test station microprocessor 132 to activate the second solenoid 56. In this condition (see FIG. 17), liquid collected in the bottle 48 drains through the drain tube 82 into the receptacle 172 provided.

In a preferred embodiment, the host program 160 uses the load cell 44 to monitor the total volume of liquid entering the bottle 48 during the liquid conveyance tests. During subsequent drainage of the bottle, the host program 160 uses the load cell 160 to monitor the volume of liquid that drains from the bottle 48. The host program 160 compares the volume of liquid that entered the bottle 48 during the tests with the volume of liquid drained from the bottle 48 after the tests. If the two volumes do not compare, the host program 160 generates an alert, prompting the operator to open the access door 112 to the wet chamber 40 and check the bottle 48 for residual liquid.

Furthermore, the host program 160 can sense when the bottle 48 fills during a given liquid conveyance test by comparing the total volume of liquid entering the bottle 48 to a preestablished value corresponding to the safe liquid capacity of the bottle 48. In this situation, the host program 160 suspends the ongoing test and directs the test station microprocessor 132 to activate the second solenoid 56 to drain the bottle 48. Following drainage, the host program 160 resumes the suspended liquid conveyance test.

(4) Electrical Safety Tests

The host program 160 carries out the electrical safety tests, if required by the test matrix 162 (see FIG. 11), by directing the test station microprocessor 132 to operate the relays on the first circuit board 122 in the dry chamber 42. The test station microprocessor 132 registers a series of measurements that test ground continuity, leakage current, and other electrical safety functions recommended or required by UL and/or AAMI.

The test station microprocessor 132 transfers these electrical measurements to the host CPU 24. The host program 160 compares these measured values to prescribed values set by the host program 160 based upon UL or AAMI standards.

The particular electrical aspects of the IV pump 20 identified for measurement during the electrical safety tests can vary according to the particular specifications of the pump 20. In the preferred embodiment, the aspects that the host program 160 includes during the electrical safety tests include:

1. Internal Leakage; AC Off; Reverse Polarity; No Ground.
2. Internal Leakage; AC Off; Reverse Polarity; With Ground.
3. Internal Leakage; AC On; Reverse Polarity; No Ground.
4. Internal Leakage; AC On; Reverse Polarity; With Ground.
5. Internal Leakage; AC Off; Normal Polarity; No Ground.
6. Internal Leakage; AC Off; Normal Polarity; With Ground.
7. Internal Leakage; AC On; Normal Polarity; No Ground.
8. Internal Leakage; AC On; Normal Polarity; With Ground.
9. External Leakage; AC Off; Reverse Polarity; No Ground.
10. External Leakage; AC Off; Reverse Polarity; With Ground.
11. External Leakage; AC On; Reverse Polarity; No Ground.
12. External Leakage; AC On; Reverse Polarity; With Ground.
13. External Leakage; AC Off; Normal Polarity; No Ground.
14. External Leakage; AC Off; Normal Polarity; With Ground.
15. External Leakage; AC On; Normal Polarity; No Ground.
16. External Leakage; AC On; Normal Polarity; With Ground.
17. Ground Wire Resistance.

If a given measured electrical value meets the specified value, the host program 160 registers a PASS result for that measured electrical value. Otherwise, the host program 160 registers a FAIL result.

If the host program 160 registers a PASS result for all measured electrical values, the host program 160 registers an overall PASS result for the electrical safety tests. If the host program 160 registers a FAIL result for any one measured electrical value, the host program 160 registers an overall FAIL result for the electrical safety tests.

Figure 28A:
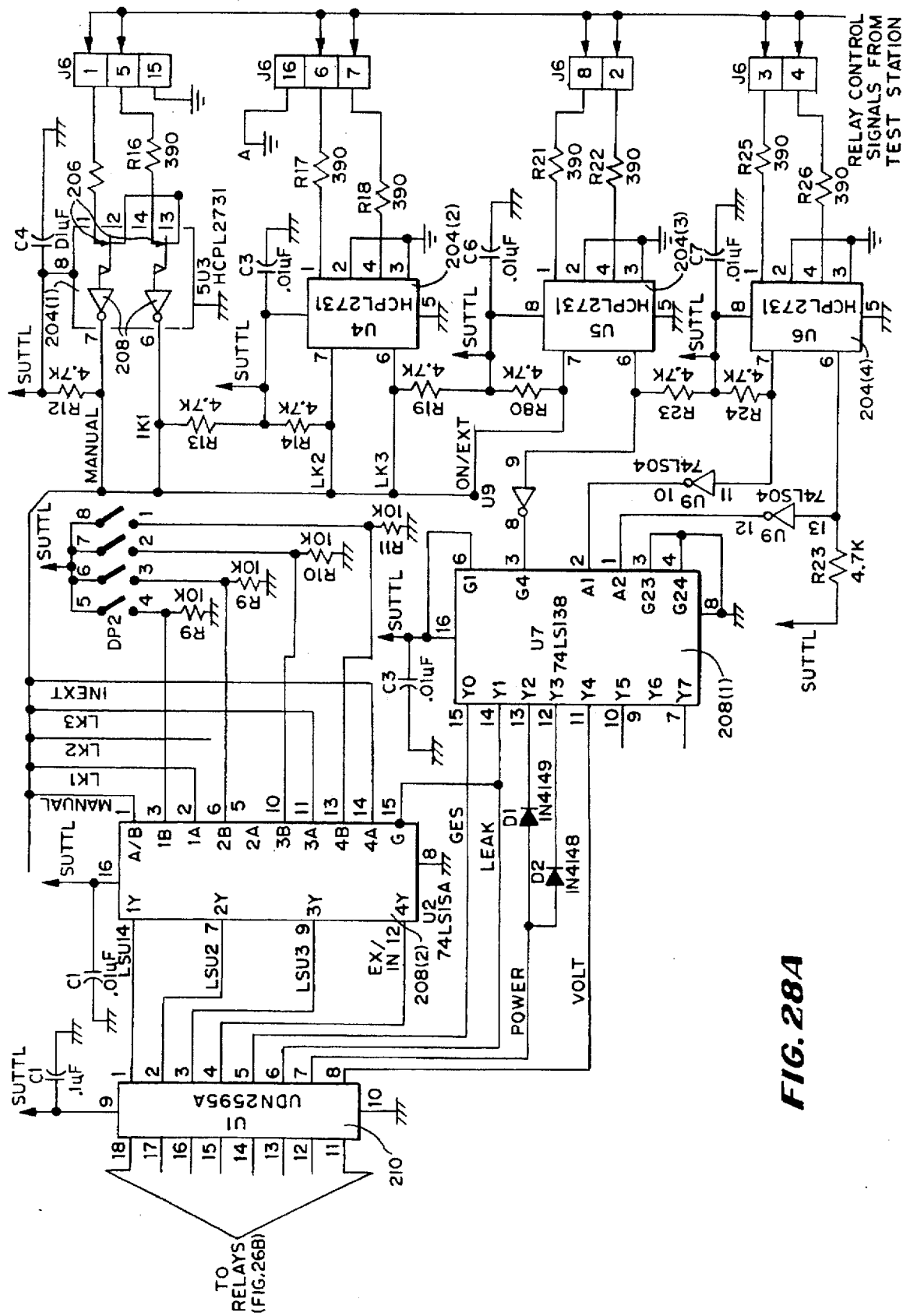
FIGS. 28A and B are schematic views of the components carried on the first circuit board (shown schematically in FIG. 6A) used to test the electrical safety characteristics of an IV pump.
Figure 28B:
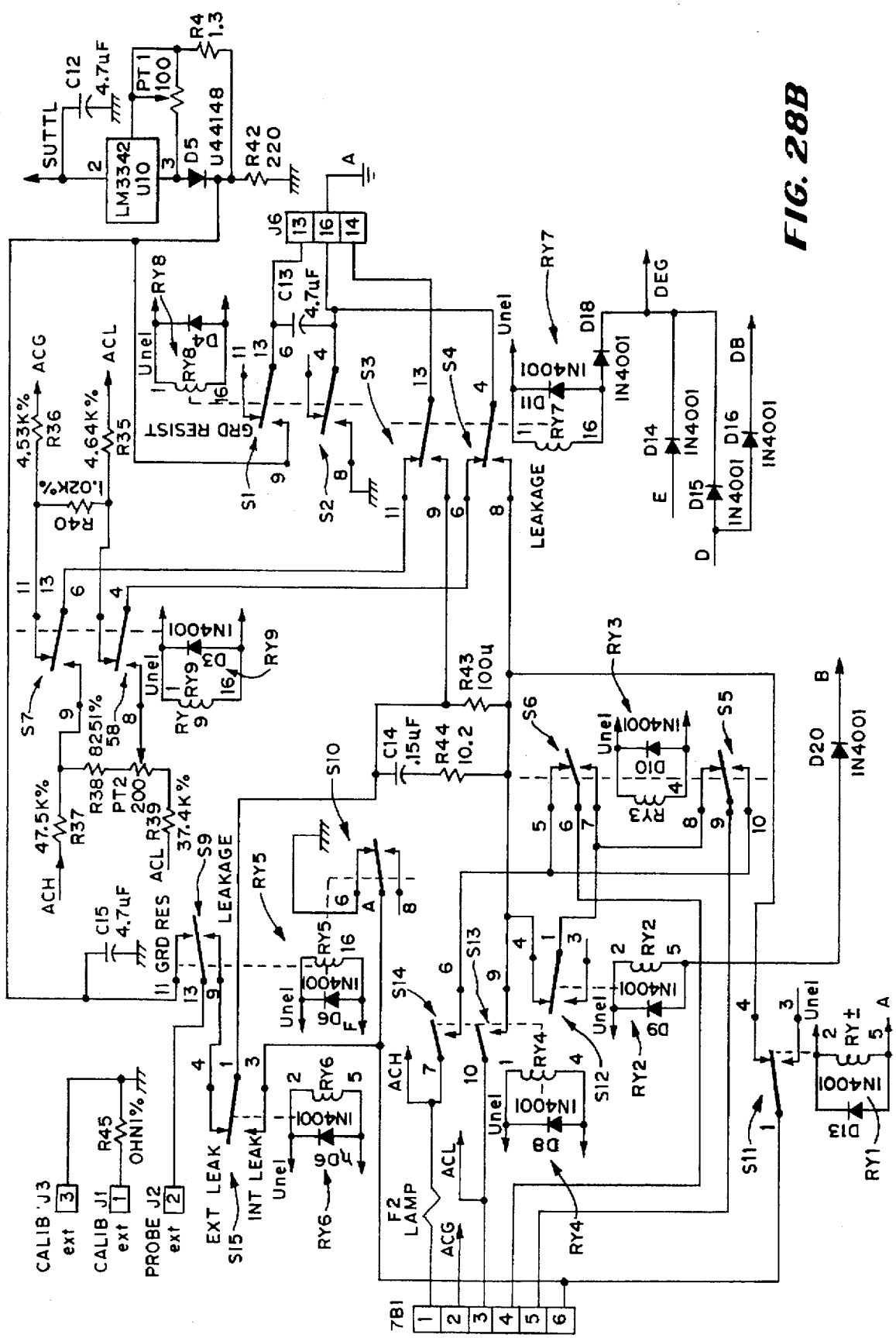

The particular construction, arrangement, and operation of electrical components 68 on the first circuit board 122 to carry out the electrical safety tests can vary. FIGS. 28A and 28B shows a preferred embodiment.

FIG. 28A shows the relay control signals generated by the test station microprocessor 132 are communicated as a digital, eight bit binary code. The code is first channeled in groups of two through four optical isolation devices 204(1); 204(2); 204(3); and 204(4). The devices 204(1)–(4) each comprises a type HCPL2731 optical isolation device. Each device converts the received bits of digital code into light signals emitted by associated LED sources 206, which are received by sensors 208. The details of this are shown only for device 204(1), although all devices 204(1) to (4) are identically constructed.

The light signals are decoded by two decoders 208(1) and (2), which are type 74LS138 and 74LS158 decoders, respectively. The decoded signals are then transmitted to a type UDN2395A relay driver 210. Based upon the (now processed and decoded) eight bit code it receives, the driver 210 activates one or more selected relays, which are shown in FIG. 28B.

There are nine relays on the first circuit board 122, identified in FIG. 28B as RY1 to RY9. The relays RY1 to RY9 are each mechanically linked to one or more switch elements, numbering fifteen and designated S1 to S15 in FIG. 28B. The linkage between a relay and a switch or switches is shown by dotted lines in FIG. 28B.

As FIG. 28B shows:

Relay RY1 is linked to switch S11.
Relay RY2 is linked to switch S12.
Relay RY3 is linked in tandem to switches S5 and S6.
Relay RY4 is linked in tandem to switches S13 and S14.
Relay RY5 is linked in tandem to switches S9 and S10.
Relay RY6 is linked to switch S15.
Relay RY7 is linked in tandem to switches S3 and S4.
Relay RY8 is linked in tandem to switches S1 and S2.
Relay RY9 is linked in tandem to switches S7 and S8.

Voltage from the power source PS1 enters the switched circuit shown in FIG. 28B through terminal TB1, pin 1 (AC Hot); pin 2 (AC Ground); and pin 3 (AC Low), which are controlled by switches S13 (AC Hot) and S14 (AC Low). The three prong pump plug outlet 144 (on the front panel 66 of the test station 12) communicates with the switched circuit through terminal TB1, pins 4, 5, and 6, which are controlled by S6; S5; and S11, respectively. Switch S10 is common to all pins 1 to 6 on terminal TB1. The external ground probe 142 of the test station is connected at terminal J2, pin 2, which is controlled by switch S9. The remaining switches further direct current flow to carry out the various electrical tests desired.

As configured in FIG. 28B, relay RY1 controls the open grid. Relay RY2 controls power on/off. Relay RY3 controls reverse polarity. Relay RY4 controls power on activate. Switch RY5 controls the selection between resistance and leakage testing. Switch RY6 control internal (test station) and external (pump) electrical testing. Switch RY7 controls the leakage signal. Switch RY8 controls the ground resistance signal. Switch RY9 controls the line voltage signal.

The relay driver 210 provides signals to activate the relays RY1 to RY9 alone or in groups to conduct the various electrical safety tests as follows:

| TST | RY 1 | RY 2 | RY3 | RY 4 | RY 5 | RY 6 | RY 7 | RY 8 | RY 9 |
|---|---|---|---|---|---|---|---|---|---|
| 1  |   |   |   |   |   |   |   | X |   |
| 2  |   |   |   | X | X |   | X |   |   |
| 3  | X |   |   | X | X |   | X |   |   |
| 4  |   | X |   | X | X |   | X |   |   |
| 5  | X | X |   |   | X |   | X |   |   |
| 6  |   |   | X | X | X |   | X |   |   |
| 7  | X |   |   | X | X |   | X |   |   |
| 8  |   | X | X | X | X |   | X |   |   |
| 9  | X | X | X | X | X |   | X |   |   |
| 10 |   |   |   | X | X | X | X |   |   |
| 11 | X |   |   | X | X | X | X |   |   |
| 12 |   | X |   | X | X | X | X |   |   |
| 13 | X | X |   | X | X | X | X |   |   |
| 14 |   |   | X | X | X | X | X |   |   |
| 15 | X |   | X | X | X | X | X |   |   |
| 16 |   | X | X | X | X | X | X |   |   |
| 17 | X | X | X | X | X | X | X |   |   |
| 18 |   | X |   | X |   |   |   |   |   |
| 19 |   | X |   | X |   |   |   |   |   |
| 20 |   |   |   |   |   |   |   |   | X |
| 21 |   |   |   |   |   |   |   |   |   |

Key to Tests by Test Number

1. Ground Resistance
2. External Leakage, AC on, Normal Polarity, Normal Ground.
3. External Leakage, AC on, Normal Polarity, Open Ground.
4. External Leakage, AC off, Normal Polarity, Normal Ground.
5. External Leakage, AC off, Normal Polarity, Open Ground.
6. External Leakage, AC on, Reverse Polarity, Normal Ground.
7. External Leakage, AC on, Reverse Polarity, Open Ground.
8. External Leakage, AC off, Reverse Polarity, Normal Ground.
9. External Leakage, AC off, Reverse Polarity, Open Ground.
10. Internal Leakage, AC on, Normal Polarity, Normal Ground.
11. Internal Leakage, AC on, Normal Polarity, Open Ground.
12. Internal Leakage, AC off, Normal Polarity, Normal Ground.
13. Internal Leakage, AC off, Normal Polarity, Open Ground.
14. Internal Leakage, AC on, Reverse Polarity, Normal Ground.
15. Internal Leakage, AC on, Reverse Polarity, Open Ground.
16. Internal Leakage, AC off, Reverse Polarity, Normal Ground.
17. Internal Leakage, AC off, Reverse Polarity, Open Ground.
18. Flow Rate Testing, AC to outlet 144 on.
19. Pressure Testing, AC to outlet 144 on.
20. AC line check AC to outlet 144 off.
21. Ground to Neutral Line Check.

In the above table, a given relay with an open box (without an "X") indicates that the switch or switches associated with the relay are in the position shown in FIG. 28B. A given relay with a filled box (with an "X") indicates that the relay is activated and the switch or switches associated with the relay occupy the alternative position shown in FIG. 28B.

(5) The Score Card

In a preferred implementation, the host program 160 provides a graphical scorecard (see FIG. 27) presenting the PASS/FAIL results for each category of test and the overall PASS/FAIL result. In FIG. 27, a check mark indicates a PASS result, while an "X" indicates a FAIL result. By clicking on a given test category, the host program displays the detailed test information for that category.

By clicking the Print button, the host program 160 generates either Pump Certification Report (see FIG. 21) (if the pump received an overall PASS result) or a Pump Failure Report (see FIG. 22) (if the pump received an overall FAIL result, as the pump in FIG. 27 did). The host program 160 also generates and prints the Detailed Test Result Report (FIGS. 23A/B).

C. Test Station Calibration

As FIG. 11B shows, the host program 160 periodically prompts the operator to calibrate certain liquid measurement and electrical components of the test station 14. The period of time between these calibrations can vary. It is presently believed that host-prompted calibration of the test station 14 should occur every day of use.

The components in the test station 14 selected for periodic calibration can vary. In the illustrated and preferred embodiment, the load cell 44, the ground probe 146, and electrical components of the test station 14 are periodically recalibrated at the prompting of the host program 160.

(1) Load Cell Recalibration

To carry out a recalibration of the load cell 44, the host program 160 prompts the operator to open the access door 112 to the wet chamber 40. The host program 160 directs the test station microprocessor 132 to transmit the load cell reading with the bottle 48 empty.

The host program 160 then prompts the operator to remove weight W1 from the bracket 118 on the door and place it on the empty bottle 48. In the illustrated and preferred embodiment, this weight W1 is 100 gr. The host program 160 directs the test station microprocessor 132 to transmit the load cell reading with the 100 gr weight present on the empty bottle 48.

The host program 160 then prompts the operator to place the other weight W2 from the door bracket 118 and place it on the first weight W1 on empty bottle 48. In the illustrated and preferred embodiment, this second weight W2 is 25 gr. The host program 160 directs the test station microprocessor 132 to transmit the load cell reading with the 125 gr weight present on the empty bottle 48.

The host program 160 linearly interpolates the load cell readings for the three weight values—zero, or tare weight, for the empty bottle 48; the 100 gr weight on the bottle 48; and the 125 gr weight on the bottle 48. The host program 160 uses the zero (tare) weight and 100 gr readings, along with the assumption of a linear output among all three readings, to mathematically adjust the load cell readings during subsequent tests.

The host program 160 preferably establishes a range for calibrated weight readings. Should the calibration weight readings fall outside the established range, the host program 160 prompts the operator that the load cell 44 requires servicing.

Upon completing load cell recalibration, the host program 160 prompts the operator to return the weights W1 and W2 to the door bracket 118.

Before conducting any subsequent flow rate accuracy tests (described above), the host program 160 queries the test station microprocessor 132 to sense the tare weight to ensure that the collection bottle is in place on the load cell 44 and the calibration weights W1 and W2 have been removed.

(2) Electrical Safety Tests

With the access door 112 to the wet chamber 40 open, the host program 160 prompts the operator to connect the ground continuity probe 146 to a selected one of the resistance studs S1 mounted in the wet chamber 40 on the dividing plate 38. One stud S1 has a known resistance of zero ohms, while the other stud S2 has a known resistance of a different value (e.g., 1 ohm).

The host program 160 directs the test station microprocessor 132 to perform a ground resistance test using the known resistance of the stud S1 to which the ground probe 146 is attached. The host program 160 directs the test station microprocessor 132 to perform a ground resistance test. The microprocessor 132 should output a ground resistance value of zero ohm.

The host program 160 then prompts the operator to connect the ground probe 146 to the other stud S2. Again, the host program 160 directs the test station microprocessor 132 to perform a ground resistance test. The microprocessor 132 should output a ground resistance value of one ohm.

If either output does not match the expected resistance value, the host CPU 32 alerts the operator that calibration of the test station by a service technician is required.

When the test station calibration tests are successfully completed, the host program 160 prompts the operator to disconnect the ground continuity probe 146 from the test studs S1 and S2 and to close the access door 112 to the wet chamber 40.

III. THE DATA REPORTING STATION

The host CPU 24 processes the acquired raw data and the PASS/FAIL results for each IV pump tested. The CPU 24 stores this information in the log file database 164. The host CPU 24 also transmits this processed data to the data reporting station 16 for printing the in form of reports.

A. The Pump Pass/Failure Report

If the IV pump receives a PASS result in all applicable visual inspection tests, flow rate accuracy tests, occlusion pressure tests, and electrical safety tests, the host CPU 24 generates and sends to the data reporting station from printing a Certification Report for the IV pump in the form shown in FIG. 21. As FIG. 21 shows, the Certification Report includes a preprinted label that can be attached to the IV pump indicating its certification and that date of certification.

Figure 22:
FIG. 22 is a representative Pump Failure Report generated by the host program based upon information containing in the log file database.

If the IV pump receives a FAIL result in some or all applicable visual inspection tests, flow rate accuracy tests, occlusion pressure tests, and electrical safety tests, the host CPU 24 generates and sends to the data reporting station a Pump Failure Report for the IV pump in the form shown in FIG. 22.

B. The Detailed Test Result Report

Both the Certification Report and the Pump Failure Report are accompanied by the Detailed Test Results Report in the form shown in FIGS. 23(a) to (d). The Detailed Test Results Report lists for each applicable visual inspection tests, flow rate accuracy tests, occlusion pressure tests, and electrical safety tests, the PASS/FAIL results, with the associated raw data supporting the result. when appropriate.

For an IV pump receiving the Pump Failure Report, a review of the associated Detailed Test Results Report pinpoints the areas where performance failed to meet established criteria. It therefore simplifies subsequent trouble shooting and repair by an qualified service representative.

C. Consolidated Database Reports

The log file database 164 is a relational database. It offers the operator the flexibility of generating a diverse number of reports, presenting the data in the database 164 in different ways.

By way of example (see FIG. 11C), the host program 162 can generate various types of certification reports, in letter, listing, summary, or detailed form. Also by way of example, the host program 162 can generate various types of database reports, such as all or any selected part of the pump log files, e.g., individually, by manufacturer, or by alpha-numeric designation.

Drawing upon the host usage database 166 in the same manner, the host program 160 can generate diverse types of accounting reports relating to the use and performance of the system 10.

Various features of the invention are set forth in the following claims.

We claim:

1. A pump testing apparatus comprising
   a housing having an interior,
   a first component in the housing interior adapted to be coupled in liquid flow communication with an external intravenous pump to test at least one liquid flow characteristic of the pump,
   a second component in the housing interior adapted to be coupled electrically to the pump to test at least one electrical characteristic of the pump, and
   a panel in the housing interior compartmentalizing the housing interior into two compartments isolated one from the other, the first component being confined solely within one of the compartments and the second component being confined solely within the other one of the compartments.

2. A pump testing apparatus comprising
   a housing having an interior,
   a first component in the housing interior adapted to be coupled in liquid flow communication with an external intravenous pump to test at least one liquid flow characteristic of the pump,
   a second component in the housing interior adapted to be coupled electrically to the pump to test at least one electrical characteristic of the pump,
   a panel in the housing interior compartmentalizing the housing interior into two compartments isolated one from the other, the first component being confined solely within a first one of the compartments and the second component being confined solely within the second one of the compartments, and
   a controller in the second one of the compartments for operating the first component and the second component.

3. An apparatus according to claim 2 wherein the controller operates in response to control signals received from an external host processor.

4. An apparatus according to claim 2
wherein the controller operates in response to control signals received from an external host processor.

5. Art apparatus according to claim 1 or
wherein the at least one liquid flow characteristic tested by the first component includes liquid flow rate.

6. An apparatus according to claim 5
wherein the first component includes a load cell to measure liquid flow rate gravimetrically.

7. An apparatus according to claim 1 or 2
wherein the at least one liquid flow characteristic tested by the first component includes liquid occlusion pressure.

8. An apparatus according to claim 7
wherein the first component includes a pressure transducer to measure liquid pressure.

9. An apparatus according to claim 1 or 2
wherein the at least one electrical characteristic tested by the second component includes a measurement of electrical safety.

10. A pump testing apparatus comprising
a housing having an interior,
a first component in the housing interior adapted to be coupled in liquid flow communication with an external intravenous pump to test liquid flow rate and pressure of liquid conveyed by the pump,
a second component in the housing interior adapted to be coupled electrically to the pump to test at least one electrical safety characteristic of the pump,
a panel in the housing interior compartmentalizing the housing interior into two compartments isolated one from the other, the first component being confined solely within one of the compartments and the second component being confined solely within the other one of the compartments, and
a controller in the second one of the compartments for operating the first component and the second component.

11. An apparatus according to claim 10
wherein the first component includes a receptacle for receiving liquid from the pump, and a load cell weighing the receptacle and the liquid it receives to measure liquid flow rate gravimetrically.

12. An apparatus according to claim 11
wherein the first component includes a valve communicating with the receptacle selectively operable to drain liquid from the receptacle.

13. An apparatus according to claim 10
wherein the first component includes a pressure transducer for sensing liquid pressure.

14. An apparatus according to claim 13
wherein the first component includes a valve selectively operable for preventing liquid flow in the first component downstream of the pressure transducer.

15. A pump testing apparatus having
a component adapted to be coupled in liquid flow communication with an external intravenous pump to test pressure of liquid conveyed by the pump, the component including
a pressure transducer for sensing liquid pressure,
an inlet adapted for attachment to pump tubing to convey liquid under pressure from the pump to the pressure transducer,
an outlet to convey liquid under pressure from the pressure transducer, and
a valve block comprising an integral body having a first interior passage coupling the inlet to the pressure transducer and a second interior passage coupling the pressure transducer to the outlet, and
a valve actuator connected to the integral body operable in a first mode to open communication between the first and second interior passages to convey liquid through the valve block under pressure from the pump for sensing by the pressure transducer and in a second mode to occlude the outlet to block liquid flow through the valve block and generate an occlusion pressure in the first interior passage for sensing by the pressure transducer.

16. An apparatus according to claim 15
wherein the inlet and pressure transducer are each coupled by pressure resistant connections to the integral body in communication with the first interior passage, and
wherein the outlet is also coupled by a pressure resistant connection to the integral body in communication with the second interior passage.

17. An apparatus according to claim 16
wherein at least one of the pressure resistant connections comprises a threaded connection.

18. An apparatus according to claim 15
wherein the component further includes a receptacle coupled to the outlet to receive liquid when the first actuator operates in its first mode and a load cell for weighing the receptacle and the liquid it receives to measure liquid flow rate gravimetrically.

19. An apparatus according to claim 18
wherein the component further includes a valve communicating with the receptacle selectively operable to drain liquid from the receptacle.

20. A system for testing an intravenous fluid pump comprising:
a test station including
a housing having an interior,
a first component in the housing interior adapted to be coupled in liquid flow communication with an external intravenous pump to test at least one liquid flow characteristic of the pump,
a second component in the housing interior adapted to be coupled electrically to the pump to test at least one electrical characteristic of the pump,
a panel in the housing interior compartmentalizing the housing interior into two compartments isolated one from the other, the first component being confined solely within a first one of the compartments and the second component being confined solely within the second one of the compartments, and
a controller in the second one of the compartments for operating the first component and the second component, and
a host processor coupled to the test station controller for generating control signals according to prescribed criteria to operate the first component and generate based thereon a first test output regarding the liquid flow characteristic tested by the first component and to operate the second component and generate based thereon a second test output regarding the electrical characteristic tested by the second component.

21. A system according to claim 20
wherein the at least one liquid flow characteristic tested by the first component includes liquid flow rate.

22. A system according to claim 21 wherein the first component includes a load cell to measure liquid flow rate gravimetrically.

23. A system according to claim 20 wherein the at least one liquid flow characteristic tested by the first component includes liquid occlusion pressure.

24. A system according to claim 23 wherein the first component includes a pressure transducer to measure liquid pressure.

25. A system according to claim 20 wherein the at least one electrical characteristic tested by the second component includes a measurement of electrical safety.

26. A system according to claim 20 and further including a reporting station coupled to the host processor for communicating at least one of the test outputs on alpha or numeric or alpha-numeric format.

27. A system according to claim 20 wherein the host processor includes memory for storing at least one of the test outputs in a database.

28. A system according to claim 27 wherein the host processor includes means for sorting the database according to specified criteria and generating a sorted output.

29. A system according to claim 28 and further including a reporting station coupled to the controller for communicating the sorted output in alpha or numeric or alpha-numeric format.

30. A pump testing apparatus comprising a housing having an interior, a first circuit component in the housing interior adapted to be coupled electrically to the pump to test at least one electrical characteristic of the pump, a second circuit component in the housing interior including a processing element for transmitting control signals to the first circuit component, at least one of the first and second circuit components including optical-isolation element for electrically isolating the first circuit component from the second circuit component, a third component in the housing interior adapted to be coupled in liquid flow communication with an external intravenous pump to test at least one liquid flow characteristic of the pump, and a panel in the housing interior compartmentalizing the housing interior into two compartments isolated one from the other, the first and second circuit components being confined solely within one of the compartments and the third component being confined solely within the other one of the compartments.

31. An apparatus according to claim 30 and wherein the processing element of the second circuit component generates control signals to operate the third component.

32. An apparatus according to claim 31 wherein the processing element operates in response to control signals received from an external host processor.

* * * * *